United States Patent
Bhide et al.

(10) Patent No.: US 6,387,926 B1
(45) Date of Patent: May 14, 2002

(54) INHIBITORS OF FARNESYL PROTEIN TRANSFERASE

(75) Inventors: Rajeev S. Bhide, Langhorne, PA (US); Charles Z. Ding, Plainsboro, NJ (US); John T. Hunt, Princeton, NJ (US); Soong-Hoon Kim, Lawrenceville, NJ (US); Katerina Leftheris, Skillman, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/087,179

(22) Filed: May 29, 1998

Related U.S. Application Data

(60) Provisional application No. 60/051,594, filed on Jul. 2, 1997.

(51) Int. Cl.[7] .............. A61K 31/47; C07D 215/00; C07D 215/16; C07D 215/20; C07D 215/36

(52) U.S. Cl. .............. 514/311; 514/312; 514/313; 514/314; 546/152; 546/153; 546/155; 546/156; 546/158; 546/159; 546/162; 546/163; 546/165; 546/167; 546/168; 546/169; 546/171; 546/174; 546/176; 546/178; 546/179; 546/180

(58) Field of Search .............. 546/152, 153, 546/155, 156, 158, 159, 162, 163, 165, 167, 168, 169, 171, 174, 176, 178, 179, 180; 514/311, 312, 313, 314

(56) References Cited

U.S. PATENT DOCUMENTS

| | | | |
|---|---|---|---|
| 4,110,536 A | 8/1978 | Havera et al. | 544/139 |
| 4,576,957 A | 3/1986 | Marsico, Jr. et al. | 514/383 |
| 4,623,377 A | * 11/1986 | Kurahashi et al. | 71/92 |
| 4,962,200 A | * 10/1990 | Kihara et al. | 544/333 |
| 5,017,584 A | 5/1991 | Hlasta | 514/314 |
| 5,284,841 A | 2/1994 | Chu et al. | 514/183 |
| 5,322,950 A | 6/1994 | Sircar et al. | 548/253 |
| 5,371,227 A | 12/1994 | Cremer et al. | 546/174 |
| 5,374,615 A | 12/1994 | Poss | 514/381 |
| 5,523,317 A | 6/1996 | Masaki et al. | 514/398 |
| 5,616,601 A | 4/1997 | Khanna et al. | 514/399 |
| 5,633,376 A | 5/1997 | Thurkauf et al. | 544/360 |
| 5,656,644 A | 8/1997 | Adams et al. | 514/341 |
| 5,716,966 A | 2/1998 | Cupps et al. | 514/312 |
| 5,726,197 A | 3/1998 | Clark et al. | 514/387 |
| 5,739,148 A | 4/1998 | Cupps et al. | 514/314 |
| 5,756,516 A | 5/1998 | Liu et al. | 514/307 |
| 5,792,783 A | 8/1998 | Tang et al. | 514/397 |

FOREIGN PATENT DOCUMENTS

| | | | | |
|---|---|---|---|---|
| EP | 173208 | * | 3/1986 | |
| EP | 198264 | * | 10/1986 | |
| EP | 485890 | * | 5/1992 | |
| EP | 618 221 A2 | | 10/1994 | C07K/5/00 |
| EP | 679642 | | 11/1995 | |
| JP | 58-52256 | * | 3/1983 | |
| JP | 61-68487 | * | 4/1986 | |
| JP | 61-280408 | * | 12/1986 | |
| JP | 0381478 | | 8/1991 | |
| WO | WO 9320099 | | 10/1993 | |
| WO | WO 9802432 | | 1/1998 | |
| WO | WO 9814192 | | 4/1998 | |

OTHER PUBLICATIONS

*Methods in Enzymology*, vol. 112, p. 309–396, edited by K. Widder, et al. (Academic Press, 1985).
*A Textbook of Drug Design and Development*, edited by Krosgaard–Larsen and H. Bundgaard, Chapter 5, "Design and Application of Prodrugs," by H. Bundgaard, p. 113–191 (1991).
H. Bundgaard, *Advanced Drug Delivery Reviews*, 8, 1–38 (1992).
H. Bundgaard, et al., *Journal of Pharmaceutical Sciences*, 77, 285 (1988).
N. Kakeya, et al., *Chem Phar Bull*, 32, 692 (1984).
J. S. Glen, et al., *Science*, 256, 1331 (1992).
V. Manne et al., *Drug Development Research*, 34, 121–137, (1995).

* cited by examiner

*Primary Examiner*—Mukund J. Shah
*Assistant Examiner*—Bruck Kifle
(74) *Attorney, Agent, or Firm*—Timothy J. Babcock

(57) ABSTRACT

Disclosed are quinoline and benzazepine derivatives that inhibit farnesyl-protein transferase (FTase) and the farnesylation of the oncogenic protein Ras. Thus, the compounds are useful as anti-cancer agents. The compounds are also useful in the treatment of diseases other than cancer.

9 Claims, No Drawings

INHIBITORS OF FARNESYL PROTEIN TRANSFERASE

RELATED APPLICATIONS

This application claims priority benefit under Title 35 §119(e) of U.S. Provisional Application Ser. No. 60/051,594, filed Jul. 2, 1997, and entitled INHIBITORS OF FARNESYL PROTEIN TRANSFERASE, the entire contents of which are incorporated herein by reference.

FIELD OF THE INVENTION

This invention relates to compounds that inhibit farnesyl-protein transferase and ras protein farnesylation, thereby making them useful as anti-cancer agents. The compounds are also useful in the treatment of diseases, other than cancer, associated with signal transduction pathways operating through ras and those associated with CAAX-containing proteins other than ras that are also post-translationally modified by the enzyme farnesyl protein transferase. The compounds also act as inhibitors of other prenyl transferases, and thus are effective in the treatment of diseases associated with other prenyl modifications of proteins.

BACKGROUND OF THE INVENTION

The mammalian ras gene family comprises three genes: H-ras, K-ras and N-ras. The ras proteins are a family of GTP-binding and hydrolyzing proteins that regulate cell growth and differentiation. Overproduction of normal ras proteins or mutations that inhibit their GTPase activity can lead to uncontrolled cell division.

The transforming activity of ras is dependent upon localization of the protein to plasma membranes. This membrane binding occurs via a series of post-translational modifications of the cytosolic ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The ras C-terminus contains a sequence motif termed a "Cys-$Aaa_1$-$Aaa_2$-Xaa" box (CAAX box), wherein Cys is cysteine, Aaa is an aliphatic amino acid, and Xaa is a serine or methionine. Farnesylation occurs on the cysteinyl residue of the CAAX box (Cys-186), thereby attaching the prenyl group on the protein via a thio-ether linkage.

BRIEF DESCRIPTION OF THE INVENTION

In accordance with the present invention, a compound of the formulas I, II

I

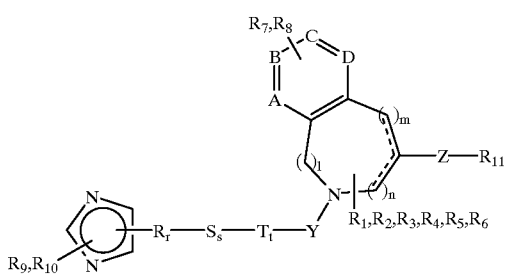

II

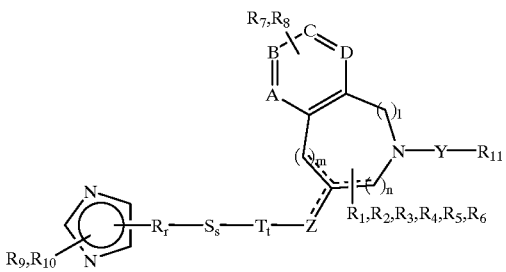

its enantiomers and diastereomers, and pharmaceutically acceptable salts, prodrugs and solvates thereof inhibit S-farnesyl protein transferase which is an enzyme involved in ras oncogene function. In formulas I and II and throughout this specification, unless otherwise specified, the symbols are defined as follows:

l, m, r, s and t are 0 or 1;

n is 0, 1 or 2;

Y is selected from the group consisting of $CHR^{12}$, $SO_2$, $SO_3$, CO, $CO_2$, O, $NR^{13}$, $SO_2NR^{14}$, $CONR^{15}$, C(NCN), $C(NCN)NR^{16}$, $NR^{17}CO$, $NR^{18}SO_2$, $CONR^{19}NR^{20}$, $SO_2NR^{21}$ $NR^{22}$, $S(O)(NR^{23})$, $S(NR^{24})(NR^{25})$, or without Y;

Z is selected from the group consisting of $CR^{12}$, S, SO, $SO_2$, $SO_3$, CO, $CO_2$, O, $NR^{13}$, $SO_2NR^{14}$, $CONR^{15}$, $NR^{26}NR^{27}$, $ONR^{28}$, $NR^{29}O$, $NR^{30}SO_2NR^{31}$, $NR^{32}SO_2$, $NR^{33}C$ (NCN), $NR^{34}C(NCN)NR^{35}$, $NR^{36}CO$, $NR^{37}CONR^{38}$, $NR^{39}CO_2$, $OCONR^{40}$, $S(O)(NR^{41})$, $S(NR^{42})(NR^{43})$ or $CHR^{12}$;

or without Z;

$R^7$, $R^8$ are selected from the group consisting of hydrogen, halo, nitro, cyano and $U-R^{44}$;

U is selected from the group consisting of S, O, $NR^{45}$, CO, SO, $SO_2$, $CO_2$, $NR^{46}CO_2$, $NR^{47}CONR^{48}$, $NR^{49}SO_2$, $NR^{50}SO_2NR^{51}$, $SO_2NR^{52}$, $NR^{53}CO$, $CONR^{54}$, $PO_2R^{55}$ and $PO_3R^{56}$ or without U;

$R^9$, $R^{10}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$ and $R^{59}$ are selected from the group consisting of hydrogen, lower alkyl, aryl, heterocyclo, substituted alkyl or aryl or substituted hetercyclo;

$R^{11}$ and $R^{44}$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo;

$R^1$, $R^2$, $R^3$, $R^4$, $R^5$ and $R^6$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo, cyano, carboxy, carbamyl (e.g. $CONH_2$), substituted carbamyl (where nitrogen may be substituted by groups selected from hydrogen, alkyl, substituted alkyl, aryl or aralkyl, substituted aryl, heterocyclo, substituted heterocyclo), alkoxycarbonyl; any two of $R^1$, $R^2$, $R^3$, $R^4$, $R^5$ and $R^6$ can join to form a cycloalkyl group; any two of $R^1$, $R^2$, $R^3$, $R^4$, $R^5$ and $R^6$ together can be oxo, except when the carbon atom bearing the substituent is part of a double bond;

R, S and T are selected from the group consisting of $CH_2$, CO and $CH(CH_2)_pQ$ wherein Q is $NR^{57}R^{58}$, $OR^{59}$, or CN; and p is 0, 1 or 2;

A, B and C are carbon, oxygen, sulfur or nitrogen; D is carbon, oxygen, sulfur or nitrogen or without D.

With the provisos that

1. When l and m are both 0, n is not 0.
2. $R^{11}$ may be hydrogen except when Z is SO, or when Z is O, $NR^{13}$ or S and the carbon to which it is attached is part of a double bond or when Y is $SO_2$, $CO_2$, $NR^{18}SO_2$, $S(O)(NR^{23})$, or $S(NR^{24})(NR^{25})$.
3. $R^{44}$ may be hydrogen except when U is SO, $SO_2$, $NR^{46}CO_2$ or $NR^{49}SO_2$.

DETAILED DESCRIPTION OF THE INVENTION

Definition of Terms

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyloxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl, aralkyl or halogen.

The term "halogen" or "halo" refers to fluorine, chlorine, bromine and iodine. The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to a optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like. Exemplary substituents include one or more alkyl groups as described above or one or more groups described above as alkyl substituents. Also included are smaller heterocyclos, such as, epoxides and aziridines. The term "heteroatoms" shall include oxygen, sulfur and nitrogen.

The "ABCD" fused ring may be monocyclic or bicyclic, e.g. napthyl or quinolyl in nature.

The compounds of formulas I–II form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formulas I–II may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be obtained, for example, by exchanging the carboxylic acid protons, if they contain a carboxylic acid, in compounds of formulas I–II with the desired ion in a medium in which the salt precipitates or in an aqueous medium followed by evaporation. Other salts can be formed as known to those skilled in the art.

The compounds for formulas I–II form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compounds of formulas I–II in an equivalent amount of the acid in a medium in which the salt precipitates or in an aqueous medium followed by evaporation.

In addition, zwitterions ("inner salts") may be formed.

Compounds of the formulas I–II may also have prodrug forms. Any compound that will be converted in vivo to provide the bioactive agent (i.e., the compound for formulas I–II) is a prodrug within the scope and spirit of the invention.

For example carboxylate ester, which are conveniently formed by esterifying any of the carboxylic acid functionalities found on the disclosed ring structure(s).

Various forms of prodrugs are well known in the art. For examples of such prodrug derivatives, see:

a) *Design of Prodrugs,* edited by H. Bundgaard, (Elsevier, 1985) and *Methods in Enzymology,* Vol.42, p. 309–396, edited by K. Widder, et al. (Acamedic Press, 1985);

b) *A Textbook of Drug Design and Development,* edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews,* 8, 1–38 (1992);

d) H. Bundgaard, et al., *Journal of Pharmaceutical Sciences,* 77, 285 (1988); and e) N. Kakeya, et al., *Chem Phar Bull,* 32, 692 (1984).

It should further be understood that solvates (e.g., hydrates) of the compounds of formulas I–II are also within the scope of the present invention. Methods of solvation are generally known in the art.

Preferred Moieties

For compounds of the present invention, the following moieties are preferred:

In compounds of Formulas I and II, n is 1 or 2.

More preferred are compounds of Formulas I and II wherein n is 1 or 2 and "ABCD" is a carbocyclic ring, e.g. benzo.

Use and Utility

The compounds of formulas I-II are inhibitors of S-farnesyl protein transferase. They are thus useful in the treatment of a variety of cancers, including (but not limited to) the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer and teratocarcinoma.

The compounds of formulas I–II are especially useful in treatment of tumors having a high incidence of ras involvement, such as colon, lung, and pancreatic tumors. By the administration of a composition having one (or a combination) of the compounds of this invention, development of tumors in a mammalian host is reduced.

Compounds of formulas I–II are also useful in the treatment of diseases other than cancer that are associated with signal transduction pathways operating through ras, e.g., neuro-fibromatosis, atherosclerosis, pulmonary fibrosis, arthritis, psoriasis, glomerulonephritis, restenosis following angioplasty or vascular surgery, hypertrophic scar formation and endotoxic shock.

Compounds of formulas I–II are also useful as anti-fungal agents.

Compounds of formulas I–II are also useful in the treatment of diseases associated with farnesyl transferase substrates other than ras (e.g., nuclear lamins and transducin) that are also post-translationally modified by the enzyme farnesyl protein transferase.

Compounds of formulas I–II also act as inhibitors of other prenyl transferases (e.g., geranylgeranyl transferase I and II), and thus can be effective in the treatment of diseases associated with other prenyl modifications (e.g., geranylgeranylation) of proteins (e.g. the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection [J. S. Glen, et al., *Science*, 256, 1331 (1992)].

Compounds of formula I–II also induce or inhibit apoptosis, a physiological cell death process critical for normal development and homeostasis. Alterations of apoptotic pathways contribute to the pathogenesis of a variety of human diseases. Compounds of formula I–II, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

The compounds of this invention are also useful in combination with known anti-cancer and cytotoxic agents, i.e. Topoisomerase I and II inhibitors, antimetabolites, agents that affect microtubules, DNA intercalaters and binders, agents that interfere with angiogenesis, DNA alkylating agents, hormonal agents, protein kinase inhibitors, ribonucleotide reductase inhibitors, mitochondrial respiratory inhibitors, agents that affect Golgi apparaus, telomerase inhibitors, prenyl transferase inhibitors, cell membrane interactive agents, and treatments, including radiation. If formulated as a fixed dose, such combination products employ the compounds of this invention within the dosage range described below and the other pharmaceutically active agent within its approved dosage range. Compounds of formulas I–II can be used sequentially with known anticancer or cytotoxic agents and treatment, including radiation when a combination formulation is inappropriate.

Farnesyl transferase assays were performed as described in V. Manne et al., *Drug Development Research*, 34, 121–137, (1995). The compounds of Examples 1–13 inhibited farnesyl transferase with IC 50 values between 1 nM and 100 uM.

The compounds of this invention can be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds are administered in a dosage range of about 0.05 to 200 mg/kg/day, preferably less than 100 mg/kg/day, in a single dose or in 2 to 4 divided doses.

Process of Preparation

Compounds of formula I or II are prepared by the following schemes.

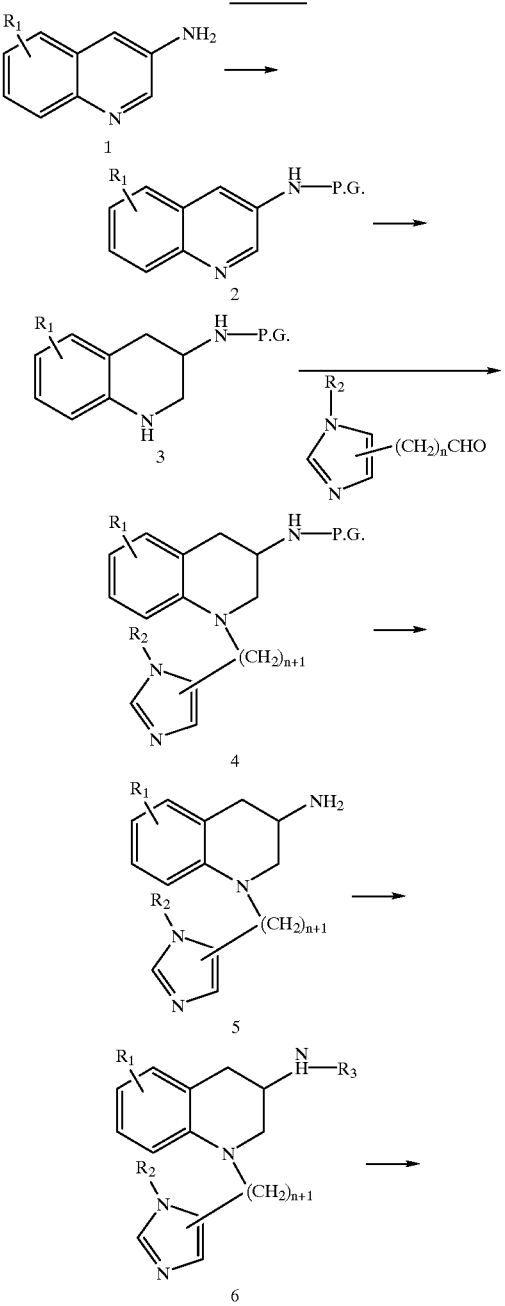

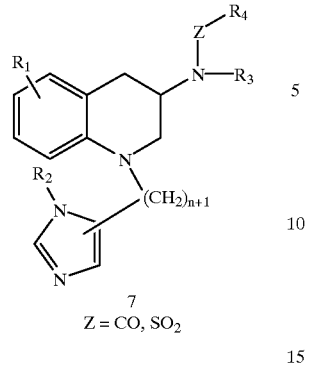

7
Z = CO, SO₂

Step 1
In Scheme 1, a compound 1 is suitably protected by, for example, a tertbutyloxycarbonyl group or a alkylsulfonyl. The reaction is carried out in an inert organic solvent e.g. THF at from −78° C. to about room temperature in the presence of a base e.g. sodium hexamethyldisilazide.

Step 2
The compound 2 is reduced via hydrogenation in the presence of a catalyst e.g. platinum oxide. The reaction is carried out in the presence of an alcohol e.g. ethanol at about room temperature.

The compound 3 wherein $R_1$ is a halogen, e.g. bromine, may be prepared from the compound 3 wherein $R_1$=H by reaction with a halogenating agent, e.g. tetrabutylammonium tribromide, in an inert solvent such as chloroform at about room temperature.

Step 3
Thereafter the various products can undergo reductive alkylation in the presence of an acid e.g. acetic acid, a reducing agent e.g. NaBH(OAc)₃ in an inert organic solvent e.g. dichloroethane at about room temperature to 60° C. Reductive alkylation may also be performed using hydrogen and a catalyst such as Pd on carbon in a solvent such as ethanol in the presence of an acid such as acetic acid at about room temperature.

Step 4
In step 4 of Scheme 1, the amine protecting group is removed (e.g., Boc by an acid such as TFA in an organic solvent such as methylene chloride).

Step 5
In step 5 of Scheme 1, the resulting compound is reacted under standard conditions with a variety of active acylating or sulfonylating agents (such as acids under carbodiimide conditions or acid chlorides to form amides; sulfonyl chlorides to form sulfonamides) to form the claimed compound 7 where $R_3$=H. Alternatively, the compound 5 is reacted under standard reductive amination conditions with aldehydes as described in Step 3 of Scheme 1 to form the compound 6 where $R_3 \neq H$. The resulting compound is reacted under standard conditions with a variety of active acylating or sulfonylating agents as descibed above to form the claimed compound 7.

Scheme 2

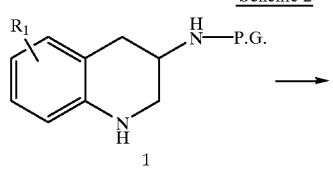

1

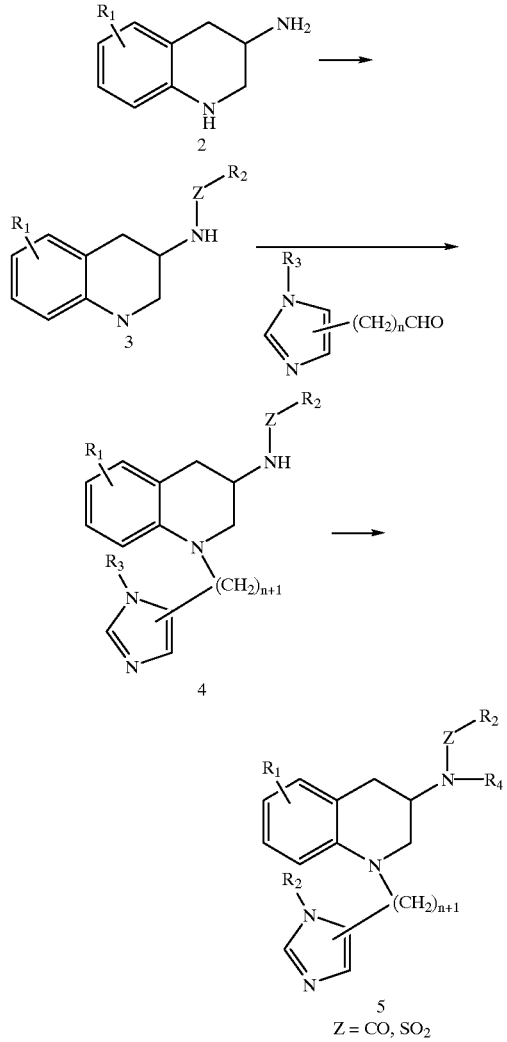

A compound 1 of scheme 2 could be obtained by the procedure described for the compound 3 of scheme 1. The amine protecting group is removed (e.g., Boc by an acid such as TFA in an organic solvent such as methylene chloride). The resulting compound 2 is reacted under standard conditions with a variety of active acylating or sulfonylating agents as described in step 5 of scheme 1 to form a compound 3. If compound 2 is treated with optically active acyl group such as mandelic acid, the resultant diastereomers could be separated by standard methods of purification such as silica gel chromatography. Removal of acylating group under standard conditions such as treatment with sulfuric acid could afford homochiral compound 2. If P.G. in compound 1 is Z-R2, then compound 4 could be obtained directly from compound 1. Thereafter, it could be reacted under standard reductive amination conditions as described in step 3 of scheme 1. The imidazole of a compound 4 is optionally protected and the resulting compound can be reacted with $R_4$-L in an inert solvent such as DMF, THF or methylene chloride in the presence of a base such as sodium hydride at from 0° C. to 100° C., where L is a leaving group such as chloride, bromide, mesylate, tosylate or triflate and $R_4$ is a substituted alkyl group, a substituted aryl group or a substituted heterocylic group. Alternatively, protected compound 4 can be treated with an alcohol under "Mitsunobu" conditions e.g. in the presence of triphenylphosphine and diethylazodicarboxylate. Thereafter, the product is deprotected e.g. in the presence of trifluoroacetic acid to obtain the claimed compound 5.

Scheme 3

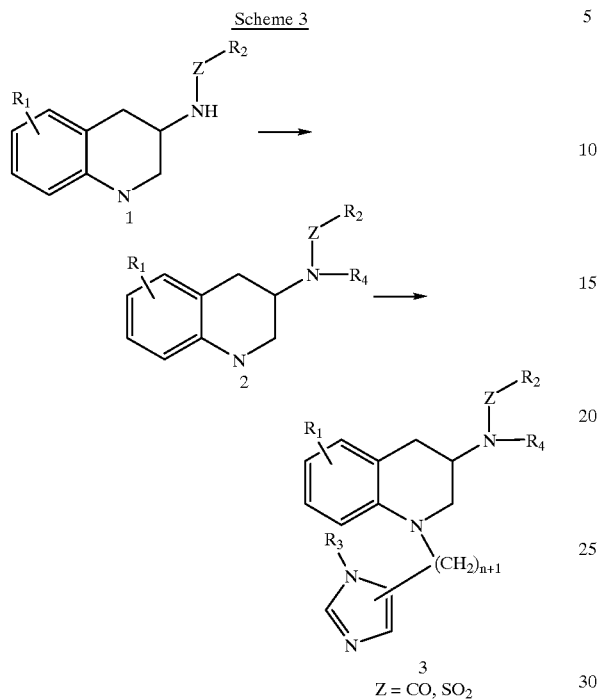

Z = CO, SO$_2$

The compound 1 of Scheme 3 wherein R$_1$ is CN can be prepared from the compound 3 of scheme 2 wherein R$_1$=halogen by displacement with CuCN in an inert solvent such as NMP at elevated temperature or with Zn(CN)$_2$ in the presence of a catalyst like tetrakistriphenylphosphine Palladium. A compound 1 of scheme 3 can be alkylated as described in step 3 of Scheme 2. Thereafter it is reacted under standard reductive amination conditions as described in step 3 of scheme 1 to obtain the claimed compound.

Scheme 4

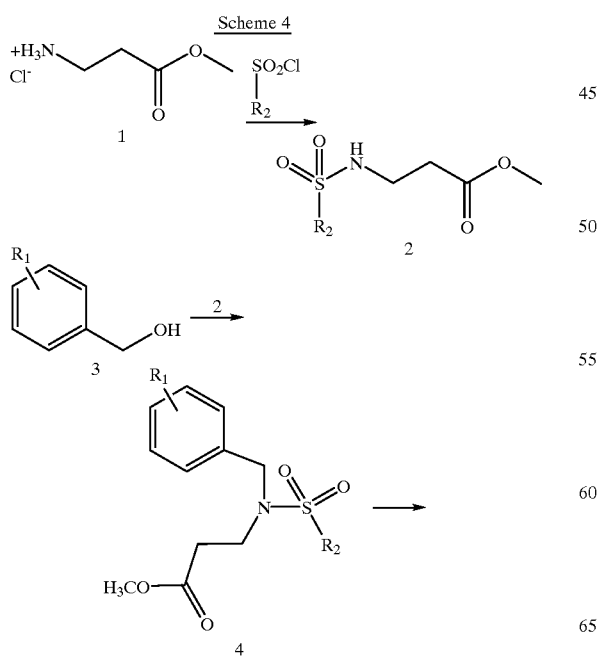

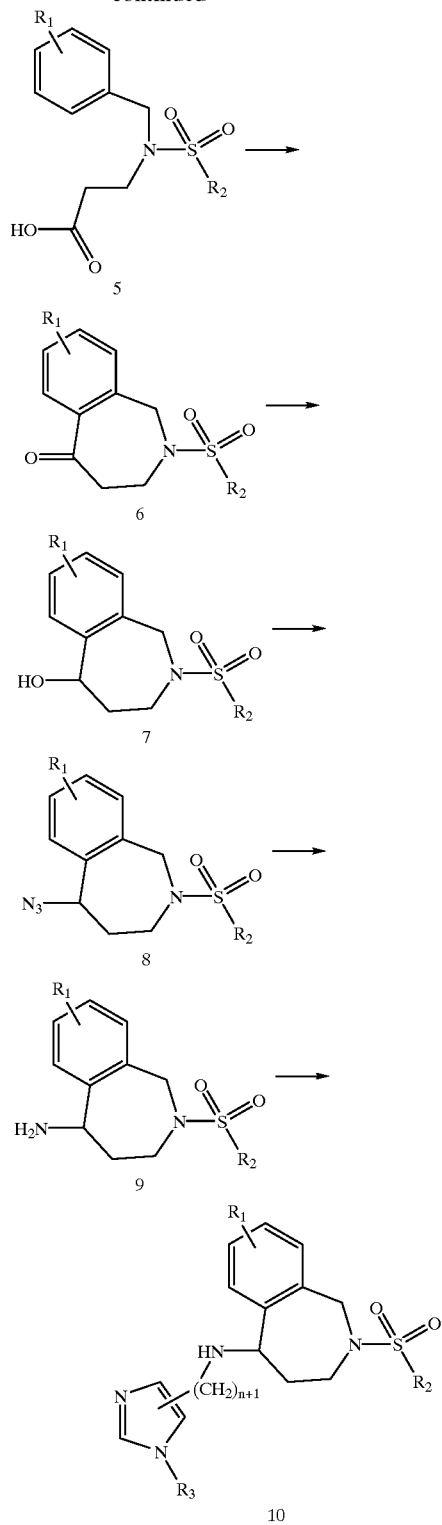

Step 1
The first step is accomplished by combining a sulfonyl chloride with the hydrochloride salt of an amino acid ester in an organic solvent in the presence of a base such as a tertiary amine at room temperature to give compound 2.
Step 2
The compound 2 is reacted with a compound 3 such as benzyl alcohol under standard Mitsunobu conditions (triphenylphosphine, diisopropylazodicarboxylate, THF as solvent) at room temperature to give compound 4. A compound 3 where $R_1$ is aryl can be prepared from a compound 3 where $R_1$ is bromo, iodo or trifluoromethanesulfonyl, by coupling of an aryl or heteroaryl metaloid derivative such as phenylboronic acid using a catalyst such as palladium acetate or tetrakis(triphenylphosphine) palladium in a mixed solvent such as water/acetone in the presence of a base such as sodium carbonate at from room temperature to 90° C.

Step 3

Thereafter, the product is saponified under basic conditions such as lithium hydroxide in a solvent such as water/THF to give a compound 5.

Step 4

Thereafter, the compound 5 is converted to the acid chloride by treatment with thionyl chloride in an organic solvent such as methylene chloride in the presence of a catalytic amount of pyridine at 35° C. The resulting acid chloride is cyclized to give the compound 6 via a Friedel-Crafts type cyclization method in the presence of a Lewis acid such as aluminum trichloride in an organic solvent such as methylene chloride.

Step 5

Thereafter, the compound 6 is reduced to the compound 7 by treatment with a reducing agent such as sodium borohydride at room temperature in a protic solvent such as ethanol.

Step 6

Thereafter, the compound 7 is converted to the compound 8 by treatment with an azide compound such as diphenylphosphorylazide in the presence of a base such as DBU in an organic solvent such as toluene at 0° C.

Step 7

Thereafter, the compound 8 is converted to the compound 9 by treatment with a reducing agent such as lithium aluminium hydride in an organic solvent such as THF.

Step 8

Thereafter, the various products can undergo reductive alkylation in the presence of an acid such as acetic acid, a reducing agent such as sodium triacetoxyborohydride and an aldehyde such as formylimidazole in an inert organic solvent such as dichloromethane at room temperature to 50° C. to give the compound 10.

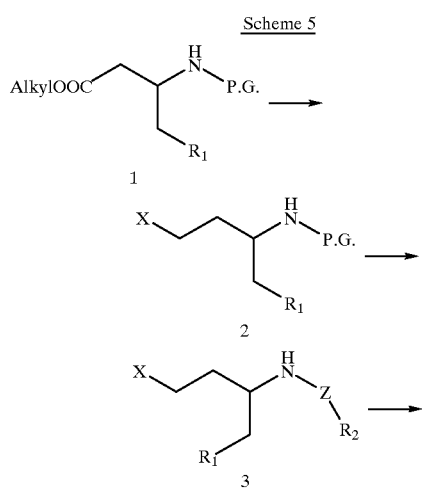

Scheme 5

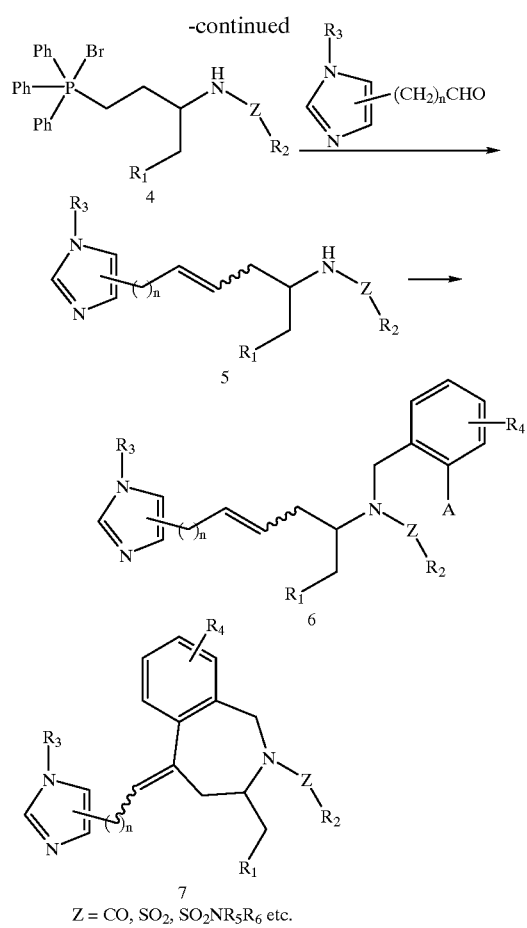

$Z = CO, SO_2, SO_2NR_5R_6$ etc.

Beta-amino ester 1, obtained from alfa-amino esters by methods known in the art, could be reduced to alcohol (X=OH) by a reducing agent such as lithium borohydride. The alcohol group could be then converted to a halogen such as bromine by methods known in the art such as carbon tetrabromide in the presence of triphenyl phosphine. The protecting group P.G. could then be removed if desired e.g. Boc group could be removed by treatment with HCl in dioxane. The free amine could be converted to sulfonamide ($Z=SO_2$) by treatment with various sulfonyl chlorides such as benzenesulfonyl chloride. Thereafter, compound 3 could be converted to a phosphonium ylide by treatment with triaryl or trialkylphosphines such as triphenylphosphine. Thereafter, ylide 4 could be treated with variously substituted imidazole aldehydes such as 1-trityl-4-formylimidazole in the presence of a strong base such as lithium hexamethyldisilazane to obtain compound 5 containing cis or trans double bond. Thereafter, compound 5 could be alkylated at nitrogen by treatment with variously substituted 2-bromotoluenes containing a leaving group on the methyl group, such as 4-Bromo-3-(bromomethyl)benzonitrile in the presence of a base such as potassium hexamethyidisilazane to afford compounds of type 6. Thereafter, a compound 6 could be cyclized in the presence of a catalyst such as palladium acetate in the presence of a base such as triethylamine to obtain compound 7. If a protecting group R3 such as triphenylmethane is used, it could be removed by treatment with an acid such as trifluoroacetic acid.

Protecting groups as used herein may be used in the above processes with amines having reactive functionalities, such as hydroxyl, carboxyl, amino, mercapto, guanidino, imidazolyl, indolyl and the like. The particular protecting groups used for any amino acid residues depend upon the other groups to be protected and are generally known in the art. Exemplary protecting groups include acetyl, benzoyl, benzyl, t-butyl and the like for hydroxyl; cyclohexyl, benzyl, methyl, ethyl, t-butyl and the like for carboxyl; benzyl, 4-methylbenzyl, 4-methoxybenzyl, acetyl, acetamidomethyl, triphenylmethyl (trityl) and the like for mercapto; t-butoxycarbonyl (Boc), benzyloxylcarbonyl (Cbz), N-[(9H-Fluoren-9-ylmethoxy)carbonyl] (Fmoc), phthaloyl (Pht), p-toluenesulfonyl (Tos), trifluoroacetyl, 2-(trimethylsilyl)ethoxycarbonyl (Teoc) and the like for amino; 2,4-dinitrophenyl, benzyloxymethyl, Tos, Boc, trityl and the like for imidazolyl; formyl, Cbz, Teoc, 2,2,2-trichloroethyl carbamate (TROC) and the like for indolyl; and tosyl, nitro, bis(1-adamantyloxycarbonyl) and the like for guanidino.

Protective groups may be removed, if desired, by, for example, treatment with one or more deprotecting agents in an inert solvent or solvent mixture. For examples of protecting groups and suitable deprotecting agents, see M. Bodansky and A. Bodansky, "The Practice of Peptide Synthesis", Springer-Verlag, Inc. (1984); and T. W. Greene and P. G. M. Wuts, "Protective Groups in Organic Synthesis", Second Edition, John Wiley & Sons, New York, 1991. The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

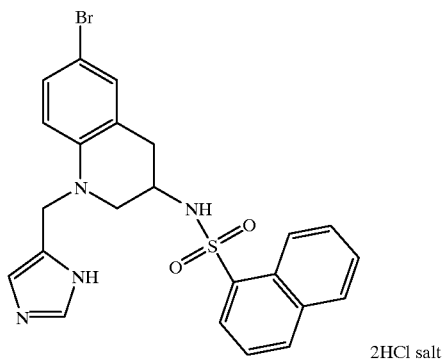

N-[6-Bromo-1,2,3,4-tetrahydro-1-(1H-imidazol-4-ylmethyl)-3-quinolinyl]-1-naphthalenesulfonamide, dihydrochloride The title compound was prepared as follows.

A) 3-Quinolinylcarbamic acid, 1,1-dimethylethyl ester

To a solution of 3-aminoquinoline (1.44 g, 10 mmol) in tetrahydrofuran (30 mL) under argon was added sodium hexamethyldisilazide (1M in tetrahydrofuran, 21 mL, 21 mmol). To the resulting dark brown mixture was added Boc anhydride (2.4 g, 11 mmol). After 1 hour, water (10 mL) and 1 N HCl (15 mL) were added to the mixture. The aqueous layer was separated, and extracted with ethyl acetate (25 mL). The combined organic layer was washed with brine (15 mL), dried (MgSO$_4$), and concentrated to afford practically pure compound A (2.5 g, 100%). MS; (M+H)$^+$=245.

B) (1,2,3,4-Tetrahydro-3-quinolinyl)carbamic acid, 1,1-dimethylethyl ester

To a solution of compound A (1.0 g, 4.1 mmol) in methanol (25 mL) were added acetic acid (3 mL) and platinum oxide (100 mg). The mixture was subjected to hydrogenation under 45 psi of pressure. After 18 hours, the mixture was filtered and the filtrate was concentrated in vacuo. The residue was dissolved in chloroform (30 mL) and washed with saturated aqueous NaHCO$_3$solution (30 mL). The organic layer was dried (MgSO$_4$), and concentrated. Purification by flash silica gel column chromatography eluting with 30% ethyl acetate in hexanes afforded compound B (460 mg, 46%) as a pale yellow solid. MS; (M−H)$^-$=247.

C) (6-Bromo-1,2,3,4-tetrahydro-3-quinolinyl)carbamic acid, 1,1-dimethylethyl ester To a solution of compound B (90 mg, 0.37 mmol) in tetrahydrofuran (2 mL) was added dropwise a solution of pyridinium tribromide (128 mg, 0.41 mmol) in tetrahydrofuran (2 mL). After 15 minutes, water and ether (5 mL each) were added. The organic layer was separated and washed with water (10 mL). The combined aqueous layer was extracted with ethyl acetate (10 mL). The organic layers were combined, dried (MgSO$_4$),, and concentrated. Purification by silica gel flash column chromatography eluting with 30% ethyl acetate in hexanes afforded compound C (90 mg, 75%) as a solid. MS; (M+H)$^+$=327 1 Br pattern.

D) [6-Bromo-1,2,3,4-tetrahydro-1-(1H-imidazol-4-ylmethyl)-3-quinolinyl]carbamic acid, 1,1-dimethylethyl ester To a solution of compound C (200 mg, 0.61 mmol) in dichloromethane (3 mL) were added 4-formylimidazole (96 mg, 1 mmol), acetic acid (0.5 mL) and 3A sieves. After 15 minutes, sodium triacetoxyborohydride (212 mg, 1 mmol) was added and the mixture was stirred vigorously. After 3 hours, the mixture was filtered through celite, and the filtrate was treated with aqueous ammonia solution (10 N, 20 mL) and chloroform (15 mL). After 1 hour, the organic layer was separated, dried (MgSO$_4$), and concentrated. The residue was purified by silica gel flash column chromatography eluting with 0.5% methanol in chloroform to afford compound D (208 mg, 93%) as a solid. MS; (M+H)$^+$=407, 409, 1 Br pattern.

E) 6-Bromo-1,2,3,4-tetrahydro-1-(1H-imidazol-4-ylmethyl)-3-quinolinamine trihydrochloride To a solution of compound D (200 mg, 0.49 mmol) in chloroform (3 mL) was added trifluoroacetic acid (1.5 mL). After 2 hours, the mixture was concentrated in vacuo. The residue was dissolved in chloroform (20 mL) and washed with 0.5 N NaOH (10 mL). The organic layer was separated, dried and concentrated to obtain the desired product (35 mg). The aqueous layer was concentrated in vacuo and the residue was triturated with methanol (2×10 mL). The methanol extracts were combined with previously obtained product and the mixture was concentrated to afford a solid (600 mg) which was dissolved in methanol (5 mL) and treated with 1 N HCl in ether (20 mL). Ether was removed on rotary evaporator and the remaining solution was filtered. The filtrate was concentrated to afford compound E (190 mg, 93%) as a yellow powder.

MS; (M+H)$^+$=307$^+$, 309$^+$, 1 Br pattern.

F) N-[6-Bromo-1,2,3,4-tetrahydro-1-(1H-imidazol-4-ylmethyl)-3-guinolinyl]-1-naphthalenesulfonamide, dihydrochloride To a suspension of compound E (50 mg, 0.12 mmol) in dichloromethane (3 mL) were added diisopropylethyl amine (0.5 mL) and 1-naphthalenesulfonyl chloride (58 mg, 0.26 mmol). After 18 hours, chloroform and saturated aqueous NaHCO$_3$ solution (10 mL each) were added to the mixture. The organic layer was separated, dried and concentrated. Purification by silica gel flash column chromatography eluting with 10% methanol in chloroform afforded bis-sulfonylated product which was dissolved in methanol (0.5 mL) and 1N NaOH (0.3 mL) was added. After 1 hour, water (2 mL) was added and the mixture was extracted with chloroform (5 mL). The organic layer was dried (K$_2$CO$_3$) and concentrated. The residue was purified by silica gel flash column chromatography eluting with 0.5% methanol in chloroform to afford the free base of the title compound (28 mg, 47%). 1N HCl in ether (2 mL) was added to this solid and the mixture was dried in vacuo to afford the title compound (30 mg). MS; (M+H)$^+$=497, 499.

R$_f$ 0.33 (10% methanol in chloroform).

EXAMPLE 2

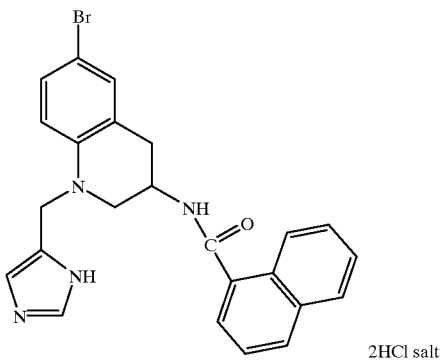

N-[6-Bromo-1,2,3,4-tetrahydro-1-(1H-imidazol-4-ylmethyl)-3-quinolinyl]-1-naphthalenecarboxamide, dihydrochloride To a solution of 6-Bromo-1,2,3,4-tetrahydro-1-(1H-imidazol-4-ylmethyl)-3-quinolinamine (30 mg, 0.072 mmol) in dimethyl formamide (1 mL) were sequentially added 1-hydroxyazabenzotriazole (19 mg, 0.15 mmol), 1-naphthoic acid (25 mg, 0.15 mmol), diisopropylethyl amine (0.7 mL, 0.4 mmol) and 1-(3-dimethylaminopropyl)-3-ethylcarbodiimide hydrochloride (28 mg, 0.15 mmol). After 18 hours, the mixture was diluted with chloroform (10 mL) and washed with saturated NaHCO$_3$ solution (10 mL). The organic layer was separated, dried and concentrated. Purification by silica gel flash column chromatography eluting with 50% ethyl acetate in hexanes followed by 1:9 methanol in chloroform afforded two fractions. More polar fraction 2 (14 mg) was the desired product and the less polar fraction 1 (35 mg) was diacylated product. Fraction 1 was dissolved in methanol (1 mL) and treated with NaOH solution (1 N, 0.2 mL). After 30 minutes, the mixture was concentrated and mixed with fraction 2 obtained above. The resulting mixture was dissolved in chloroform (10 mL) and washed with water (10 mL). The organic layer was dried (MgSO$_4$), concentrated and purified by silica gel flash column eluting with 5% methanol in chloroform to afford the free base of the title compound (20 mg, 60%). The solid was dissolved in chloroform and HCl gas was bubbled for 30 seconds. The mixture was then concentrated in vacuo to afford the title compund (23 mg). MS: (M+H)$^+$=461, 463 (1:1 ratio), 1 Br pattern.

IR: 1638,1499 cm$^{-1}$.

EXAMPLE 3

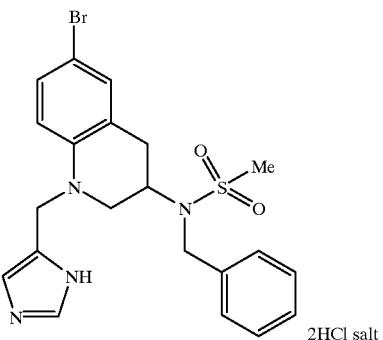

N-[6-Bromo-1,2,3,4-tetrahydro-1-(1H-imidazol-4-ylmethyl)-3-quinolinyl]-N-(phenylmethyl) methanesulfonamide, dihydrochloride The title compound was prepared as follows.

A) 6-Bromo-1,2,3,4-tetrahydro-1-(1H-imidazol-4-ylmethyl)-N-(phenylmethyl)-3-quinolinamine To a solution of 6-Bromo-1,2,3,4-tetrahydro-1-(1H-imidazol-4-ylmethyl)-3-quinolinamine (184 mg, 0.45 mmol) in methanol (2 mL) and chloroform (2 mL) at room temperature were added benzaldehyde (0.45 mL, 0.45 mmol), acetic acid (0.5 mL) and anhydrous MgSO$_4$ (1 g). After 15 minutes, sodium triacetoxyborohydride (110 mg, 0.5 mmol) was added. After 1 hour and 5 hours periods, sodium triacetoxyborohydride (215 mg and 110 mg respectively) was added. After 6 hours, the mixture was filtered and concentrated. The residue was diluted with chloroform (20 mL) and stirred vigorously with ammonium hydroxide (20 mL). After 1 hour, the aqueous layer was separated and extracted with chloroform (15 mL). The combined organic layer was dried (K$_2$CO$_3$) and concentrated in vacuo to afford compound A (120 mg, 67%) as an oil.

MS: (M+H)$^+$=397.

B) N-[6-Bromo-1,2,3,4-tetrahydro-1-(1H-imidazol-4-ylmethyl)-3-quinolinyl]-N-(phenylmethyl) methanesulfonamide dihydrochloride Compound A (40 mg, 0.1 mmol) was converted to Compound B in a manner similar to the procedure described in step F of Example 1 except, the residue obtained from work up of the reaction mixture was treated with 50% trifluoroacetic acid in dichloromethane (1 mL). After 2 hours, the mixture was concentrated and was purified by RP HPLC eluting with 40–90% aqueous methanol containing 0.1% trifluoroacetic acid. Appropriate fractions were collected, concentrated and treated with 4N HCl in dioxane (1 mL) and concentrated in vacuo. The latter procedure was repeated twice and finally the residue was dissolved in water and lyophilized to afford the title compound (10 mg, 18%). MS; (M+H)$^+$=475, 1 Br pattern.

EXAMPLE 4

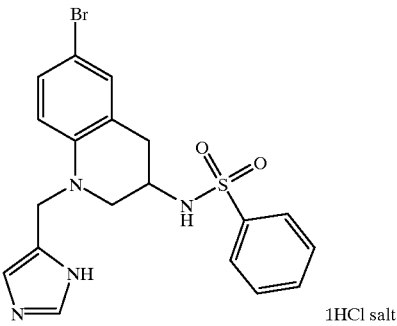

1HCl salt

N-[6-Bromo-1,2,3,4-tetrahydro-1-(1H-imidazol-4-ylmethyl)-3-quinolinyl]benzenesulfonamide, dihydrochloride The title compound was prepared in a manner similar to step F of Example 1. Thus, 6-Bromo-1,2,3,4-tetrahydro-1-(1H-imidazol-4-ylmethyl)-3-quinolinamine (42 mg, 0.1 mmol) in dimethylformamide (0.2 mL) was treated with triethylamine (0.3 mL, 2.1 mmol), dimethylaminopyridine (10 mg) and benzenesulfonyl chloride (0.014 mL, 0.11 mmol) to afford a solid (17 mg, 32%). MS; $(M+H)^+=447$, 1 Br pattern.

EXAMPLE 5

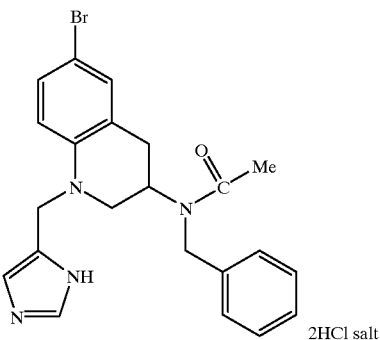

2HCl salt

N-[6-Bromo-1,2,3,4-tetrahydro-1-(1H-imidazol-4-ylmethyl)-3-quinolinyl]-N-(phenylmethyl) acetamide, dihydrochloride To a solution of compound A Example 3 (50 mg, 0.12 mmol) in pyridine (0.4 mL) at room temperature were added dimethylaminopyridine (10 mg) and acetic anhydride (0.3 mL). After 18 hours, chloroform (15 mL) and pH 4 phosphate buffer solution (10 mL) were added to the mixture. The organic layer was separated, washed with water (10 mL), dried ($K_2CO_3$) and concentrated in vacuo. The residue was purified by reverse phase (RP) HPLC eluting with 40–90% aqueous methanol containing 0.1% trifluoroacetic acid. Appropriate fractions were collected, concentrated and treated with 1N HCl and methanol (1 mL each) and then concentrated in vacuo. The latter procedure was repeated twice and finally the residue was dissolved in water and lyophilized to afford the title compound (10 mg, 20%). MS; $(M+H)^+=439$, 441, 1 Br pattern.

EXAMPLE 6

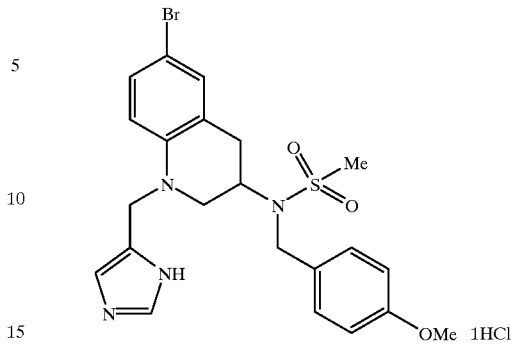

1HCl

N-[6-Bromo-1,2,3,4-tetrahydro-1-(1H-imidazol-4-ylmethyl)-3-quinolinyl]-N-(4-methoxyphenyl) methyl]methanesulfonamide, dihydrochloride The title compound was prepared as follows.
A) 6-Bromo-1,2,3,4-tetrahydro-3-quinolinamine
To a solution of (6-Bromo-1,2,3,4-tetrahydro-3-quinolinyl)carbamic acid, 1,1-dimethylethyl ester (652 mg, 2 mmol) in dichloromethane at RT under argon was added trifluoroacetic acid (1 mL). After 3 hours, the mixture was concentrated. Chloroform (10 mL) was added and concentrated again in vacuo to afford the title compound (1 g), an oil, which was used without further purification. MS; $M(+H)^+=227$.
B) N-(6-Bromo-1,2,3,4-tetrahydro-3-quinolinyl)methanesulfonamide
The title compound (400 mg, 66% over two steps) was obtained from Compound A (2 mmol crude) as an off-white solid in a manner similar to step B of Example 3. MS; $(M+H)^+=305$, 307, 1 Br pattern.
C) N-[6-Bromo-1,2,3,4-tetrahydro-1-(1H-imidazol-4-ylmethyl)-3-quinolinyl]methanesulfonamide
The title compound was prepared in a manner similar to step D of Example 1 to afford a solid (320 mg, 69%). MS; $(M+H)^+=385$, 387, 1 Br pattern.
D) N-[6-Bromo-1,2,3,4-tetrahydro-1-[[1-(triphenylmethyl)-1H-imidazol-4-yl]methyl]-3-quinolinyl]methanesulfonamide
To a solution of compound C (280 mg, 0.78 mmol) in acetonitrile (4 mL) at room temperature under argon was added diisopropylethyl amine (0.18 mL, 1 mmol) and trityl chloride (223 mg, 0.8 mmol). After stirring overnight (16 hours), the mixture was concentrated in vacuo. The residue was dissolved in chloroform (20 mL) and washed with saturated sodium bicarbonate (20 mL). The organic layer was dried ($MgSO_4$), and concentrated to afford crude compound D (500 mg, 105%) which was used without further purification. MS: $(M+H)^+=627$; $(M-H)^-=625$.
E) N-[6-Bromo-1,2,3,4-tetrahydro-1-(1H-imidazol-4-ylmethyl)-3-quinolinyl]-N-(4-methoxyphenyl)methyl]-methanesulfonamide, monohydrochloride
To a solution of compound D (63 mg, 0.1 mmol) in tetrahydrofuran (1 mL) were added triphenylphosphine (52 mg, 0.2 mmol), diisopropylazodicarboxylate (26 µL, 0.13 mmol), and 4-methoxybenzenemethanol (18 mg, 0.13 mmol). After 18 hours, another equivalent of triphenylphosphine, diisopropylazodicarboxylate and the 4-methoxybenzenemethanol were added. After 5 hours, the mixture was concentrated in vacuo and the residue was purified by silica gel flash column chromatography eluting with 50% ethyl acetate in hexanes to afford impure product. The impure product was dissolved in dichloromethane (2 mL) and treated with trifluoroacetic acid (1 mL). After 2 hours, the mixture was concentrated and the residue was purified by RP HPLC eluting with 35% to 90% aqueous methanol containing 0.1% trifluoroacetic acid. The appropriate fractions were collected, concentrated and the residue was dissolved in 1N HCl and the mixture was concentrated again. After repeating the latter step twice the residue thus obtained was dissolved in water and lyophilized to afford the title compound (14 mg, 26%).

MS; $(M+H)^+$=505, 507 in 1:1 ratio.

EXAMPLE 7

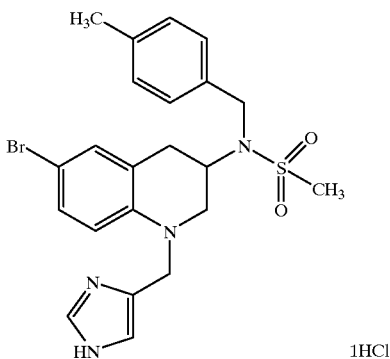

1HCl

N-[6-Bromo-1,2,3,4-tetrahydro-1-(1H-imidazol-4-ylmethyl)-3-quinolinyl]-N-[(4-methylphenyl)methyl] methanesulfonamide monohydrochloride The title compound was prepared as follows.
A) N-[6-Bromo-1,2,3,4-tetrahydro-1-[[1-(triphenylmethyl)-1H-imidazol-4-yl]methyl]-3-quinolinyl]-N-[(4-methylphenyl)-methyl]methanesulfonamide Sodium hydride (60% dispersion in oil, 7 mg, 0.17 mmol) was added to a stirred solution of compound D of Example 6 (0.1 g, 0.16 mmol) in dimethylformamide (1 mL), under argon. After stirring for 30 min, 4-methylbenzylbromide (0.035 g, 0.191 mmol) was added, and stirred over night. After 16 hours, the mixture was diluted with water (5 mL) and ethyl acetate (20 mL). The layers were separated. The aqueous layer was reextracted with ethyl acetate (2×20 mL). The combined organic extract was washed with water (2×5 mL), dried (MgSO$_4$), filtered and concentrated. The brown oil was purified on a silica gel flash column eluting with ethyl acetate and the appropriate fractions were concentrated to afford the title compound (60 mg, 52%) as a white foam.

HPLC: Rt. 4.41 min, 10–90% aqueous methanol with 0.2% H$_3$PO$_4$ buffer, 4 minutes gradient, 4 ml/min, 220 nm, YMC S5 ODS column.
B) N-[6-Bromo-1,2,3,4-tetrahydro-1-(1H-imidazol-4-ylmethyl)-3-guinolinyl]-N-[(4-methylphenyl)methyl] methane-sulfonamide, monohydrochloride Trifluoroacetic acid (0.5 mL) was added to a solution of compound A (60 mg, 0.081 mmol) in dry methylene chloride (0.5 mL) under argon. After 3 hours, the reaction was concentrated, chloroform (3 mL) was added and concentrated again. The residue was purified on a silica gel flash column eluting with 19/1 chloroform and methanol. Appropriate fractions were concentrated, the residue was treated with 1 N aqueous HCl and methanol and concentrated. This process was repeated twice. The final residue was dissolved in water and lyophilized to afford the title compound (17 mg, 43%) as a light tan solid. MS: $[M+H]^+$=489.

EXAMPLE 8

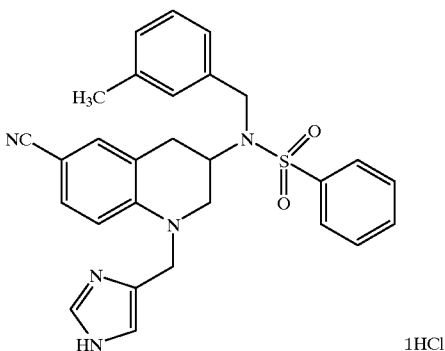

1HCl

N-[6-Cyano-1,2,3,4-tetrahydro-1-(1H-imidazol-4-ylmethyl)-3-quinolinyl]-N-[(3-methylphenyl)methyl] benzenesulfonamide monohydrochloride The title compound was prepared as follows.
A) N-(6-Bromo-1,2,3,4-tetrahydro-3-quinolinyl)benzenesulfonamide The title compound (680 mg, 56%, white solid) was prepared from 6-Bromo-1,2,3,4-tetrahydro-3-quinolinamine in a manner similar to step B of Example 3. MS: $(M+H)^+$= 366, 368 (1:1 ratio).

Alternatively, Compound A could be prepared from N-(1,2,3,4-Tetrahydro-3-Quinolinyl)benzenesulfonamide using the procedure described in this step.

N-(1,2,3,4-Tetrahydro-3-Quinolinyl)benzenesulfonamide is prepared as described in steps C and D below.
B) N-(6-Cyano-1,2,3,4-tetrahydro-3-quinolinyl)benzenesulfonamide Argon was bubbled through a solution of compound A (443 mg, 1.2 mmol) in dimethylformamide (4 mL) for 4 minutes. Zinc cyanide (135 mg, 1.15 mmol) was added and the mixture was deoxygenated. Palladium tetrakistriphenylphosphine (105 mg, 0.09 mmol) was added and the solution was deoxygenated. The mixture was then heated at 900C for 4 hours. The mixture was cooled to room temperature, and water and ethyl acetate (20 mL each) were added. The aqueous layer was separated and extracted with ethyl acetate (20 mL). The combined organic layer was dried (MgSO$_4$), filtered and concentrated in vacuo. Dichloromethane (4 mL) was added to the residue and upon standing compound B (300 mg, 81%) precipitated out as a white crystalline solid. MS; $(M+H)^+$=314.
C) N-(3-Quinolinyl)benzenesulfonamide To a solution of 3-aminoquinoline (7.2 g, 50 mmol) in acetonitrile (150 mL) was added pyridine (25 mL) and the resulting mixture was cooled to 0° C. A solution of benzenesulfonyl chloride (7 mL, 55 mmol) in acetonitrile (20 mL) was added dropwise over 30 minutes. The mixture was allowed to warm to rt and stirred for 18 hours. The mixture was diluted with ethyl acetate (100 mL) and washed successively with 1N HCl, brine and saturated CuSO$_4$, dried (MgSO$_4$), and concentrated in vacuo to afford an oil. Purification by flash silica gel column chromatography eluting with 30% ethyl acetate in hexanes afforded compound C (13. g g, 95%) as a white solid.

MS; $(M+H)^+$=285.
D) N-(1,2,3,4-Tetrahydro-3-Quinolinyl)benzenesulfonamide

To a solution of compound C (13.6 g, 4.78 mmol) in a mixture of methanol and ethyl acetate (6 and 18 mL respectively) was added 20% palladium hydroxide on carbon (1.2 g) and the mixture was subjected to hydrogenation at atmospheric pressure. After 24 hours, the mixture was filtered and the filtrate was concentrated in vacuo to afford compound B (13.6 g, 99.8%) as a white solid. MS; $(M+H)^+$= 289.

E) N-(6-Cyano-1,2,3,4-tetrahydro-3-quinolinyl)-N-[(3-methylphenyl)methyl]benzenesulfonamide Compound B (65 mg, 0.26 mmol) was converted to the title compound (34 mg, 32%) as a clear oil in a manner similar to the preparation of compound A of Example 7 except, using 3-methylbenzyl bromide (0.041 mL, 0.31 mmol). HPLC: Rt. 4.3 min, 10–90% aqueous methanol with 0.2% $H_3PO_4$ buffer, 4 minutes gradient, 4 ml/minutes, 220 nm, YMC S5 ODS column.

F) N-[6-Cyano-1,2,3,4-tetrahydro-1-(1H-imidazol-4-ylmethyl)-3-guinolinyl]-N-[(3-methylphenyl)methyl]benzene-sulfonamide, monohydrochloride A mixture of compound F (34 mg, 0.081 mmol) and 4-formylimidazole (0.31 g, 0.325 mmol) and 3A molecular sieves in dichloroethane and acetic acid (0.5 mL each) under argon was warmed to 50° C. After 2 hours, sodium triacetoxyborohydride (0.017 g, 0.479 mmol) was added. An equivalent of sodium triacetoxyborohydride was added twice at 1 hours interval. Then the mixture was cooled to room temperature and stirred over night. More borohydride and aldehyde were addeed and warmed to 50° C. After 24 hours the reaction mixture was diluted with $NH_4OH$ (2 mL) and chloroform (5 mL), and after stirring for 20 min, the layers were separated. The aqueous layer was reextracted with chloroform (2×10 mL). The combined organic layer was washed with $NaHCO_3$ (1×5 mL), dried ($MgSO_4$), filtered and concentrated. The residue was purified on a silica gel flash column eluting with ethyl acetate followed by 19/1 chloroform/methanol. Appropriate fractions were concentrated, treated with 1N aqueous HCl/methanol and then concentrated. This process was repeated twice, the residue was dissolved in water and lyophilized to afford the title compound (18 mg, 45%) as a light yellow solid. MS: $[M+H]^+$=498.

EXAMPLE 9

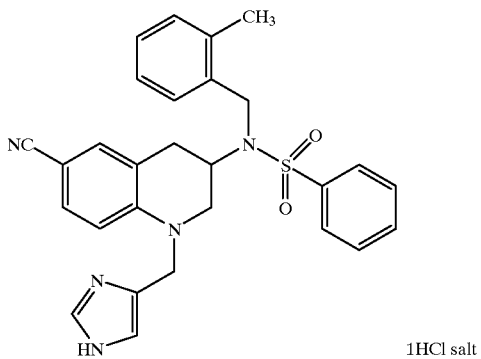

N-[6-Cyano-1,2,3,4-tetrahydro-1-(1H-imidazol-4-ylmethyl)-3-quinolinyl]-N-[(2-methylphenyl)methyl]benzenesulfonamide monohydrochloride The title compound was prepared from N-(6-Cyano-1,2,3,4-tetrahydro-3-quinolinyl)benzenesulfonamide using the procedures described in steps F and G for the preparation of Example 8, to afford a light yellow solid (39 mg, 66%). MS: $[M+H]^+$=498.

EXAMPLE 10

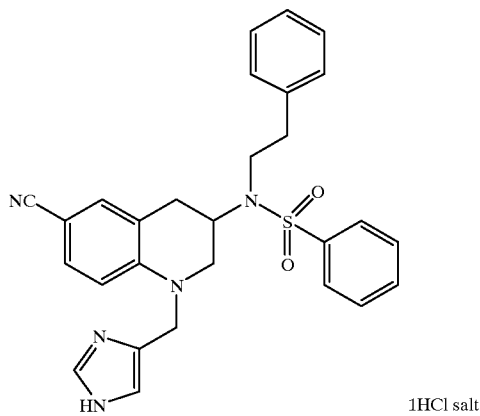

N-[6-Cyano-1,2,3,4-tetrahydro-1-(1H-imidazol-4-ylmethyl)-3-quinolinyl]-N-(phenylethyl)benzenesulfonamide monohydrochloride The title compound was prepared as follows.

A) N-(6-Cyano-1,2,3,4-tetrahydro-3-quinolinyl)-N-(phenylethyl)benzenesulfonamide A solution of N-(6-Cyano-1,2,3,4-tetrahydro-3-quinolinyl)benzene-sulfonamide (50 mg, 0.2 mmol) in dry tetrahydrofuran (2 mL) was stirred under argon. Triphenylphosphine (0.156 g, 0.596 mmol), phenethyl alcohol (0.023 mL, 0.2 mmol) and diethylazodicarboxylate (0.077 mL, 0.5 mmol) were added sequentially. After 16 hours, another equivalent of phenethyl alcohol was added. After 48 hours, the reaction was concentrated. The crude product from another reaction (obtained from the reaction of 0.24 mmol of compound B of Example 8) was mixed with this one and purified on a silica gel column eluting with hexane/ethyl acetate (3/1,2/1,1/1). The appropriate fractions were concentrated to afford impure compund A (0.1 g, 25%, only 50% pure).

MS: $[M-H]^-$=416$^-$. LC/MS: $[M+H]^+$=418.

B) N-[6-Cyano-1,2,3,4-tetrahydro-1-(1H-imidazol-4-yl-methyl)-3-quinolinyl]-N-(phenylethyl)benzenesulfonamide monohydrochloride A mixture of compound A (50 mg, 0.119 mmol), 4-formylimidazole (37 mg, 0.4 mmol) and triethylsilane (0.35 mL, 2.19 mmol) in trifluoroacetic acid and methylene chloride (each 0.7 mL) was stirred under argon. After 2 hours, the mixture was concentrated. The residue was purified on a silica gel flash column eluting with ethyl acetate followed by 19/1 chloroform/methanol. Appropriate fractions were concentrated. The residue was treated with 1N aqueous HCl/methanol and then concentrated. This process was repeated twice. Finally the residue was dissolved in water and lyophilized to afford the title compound (12 mg, 20%) as a light yellow solid. MS; $[M+H]^+$=498.

EXAMPLE 11

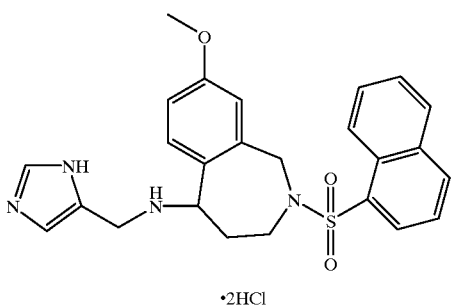

·2HCl 2,3,4,5-Tetrahydro-5-[(1H-imidazol-4-ylmethyl) amino]-2-(1-naphthylsulfonyl)-8-methoxy-1H-2-benzazepine, dihydrochloride The title compound was prepared as follows.

A) N-(1-naphthylsulfonyl)-β-alanine methyl ester

To a stirred suspension of HCl salt of beta-alanine methyl ester (6.0 g, 43 mmol) in anhydrous methylene chloride (30 mL) was added triethylamine (6 mL) followed by 1-naphthalenesulfonyl chloride (10 g, 44 mmol). After 3 hours, the solution was washed with saturated aqueous sodium bicarbonate followed by 1 M aqueous potassium bisulfate and brine. The organic layer was dried (MgSO$_4$), and concentrated in vacuo to give compound A (6.3 g, 86%) as a white solid. MS; (M+H)$^+$=294.

B) 3-N-(3-methoxybenzyl)-N-(1-naphthylsulfonyl)-β-alanine methyl ester

In dry tetrahydrofuran (10 mL) were combined m-methoxybenzyl alcohol (422 mg, 3.1 mmol), compound A (0.9 g, 3.1 mmol) and triphenylphosphine (0.8 g, 3.1 mmol). The solution was stirred under nitrogen while diisopropylazodicarboxylate (620 mg, 3.1 mmol) in tetrahydrofuran (1 mL) was added dropwise over 1 minute. The solution was stirred for 2 hours followed by concentration. The residue was purified by flash chromatography eluting with ethyl acetate:hexanes (1:10–10:0). The appropriate fractions were collected and concentrated to give compound B (1.2 g, 94%) as a white solid. MS: (M+NH$_4$)$^+$=431.

C) 3-N-(1-naphthylenylsulfonyl)-3-N-(3-methoxybenzyl) amino propionic acid

Compound B (1.1 g, 2.4 mmol) was combined with methanol (20 mL) and aqueous LiOH (6 mL, 1 M). After 16 hours, the solution was concentrated in vacuo. To the residue were added water (30 mL) and ethyl ether (30 mL) and the layers were separated. The aqueous layer was washed with ethyl ether/hexanes. The aqueous layer was acidified to pH 2 with 5N HCl (aq) and the product was extracted into ethyl acetate. The ethyl acetate layer was dried (MgSO$_4$), and concentrated to give compound C (960 mg, 99%) as a white solid. MS: (M+NH$_4$)$^+$=417.

D) 2,3,4,5-tetrahydro-8-methoxy-2-(1-naphthylsulfonyl)-2-benzazepin-5-one

To a solution of compound C (600 mg, 1.5 mmol) in methylene chloride (5 mL) was added thionyl chloride (0.3 mL, 4 mmol) and pyridine (0.001 mL) and the solution was stirred at 35° C. for 1 hour. The solution was concentrated and the residue was dissolved in methylene chloride (10 mL). After cooling the mixture to 0° C., aluminum trichloride (220 mg, 1.7 mmol) was added. After 15 minutes, the mixture was poured into 2 N aqueous HCl/ice (80 mL) along with methylene chloride (30 mL). The organic layer was separated, concentrated, dissolved in ethyl acetate (60 mL), washed with saturated aqueous sodium bicarbonate, dried (MgSO$_4$), filtered and concentrated under high vacuum to give compound D (530 mg, 92%) as off-white crystals. MS: (M+NH$_4$)$^+$=417.

E) 2,3,4,5-tetrahydro-8-methoxy-2-(1-naphthylsulfonyl)-1H-2-benzazepin-5-ol

To a solution of compound D (225 mg, 0.59 mmol) in ethanol (15 mL) was slowly added sodium borohydride (111 mg, 3 mmol). After 1 hour, ethyl acetate (60 mL) and water (60 mL) were added and the layers were separated. The aqueous layer was washed with ethyl acetate, the organic layers were combined, dried (MgSO$_4$), filtered and concentrated to give compound E (228 mg, 99%) as a glass.

MS: (M+H)$^+$=384.

F) 2,3,4,5-tetrahydro-8-methoxy-2-(1-naphthylsulfonyl)-1H-2-benzazepin-5-azide

To a cooled (0° C.) solution of compound E (200 mg, 0.52 mmol) and diphenylphosphorylazide (0.14 mL, 0.62 mmol) in dry toluene (1 mL) was added DBU (0.93 mL, 0.63 mmol). The solution was stirred for 2 hours at 0° C. and at room temperature for 16 hours. Water (20 mL), 1N aqueous HCl (5 mL) and ethyl acetate (20 mL) were added and the layers were separated. The organic layer was dried (Na$_2$SO$_4$), filtered and concentrated. The residue was purified by flash chromatography eluting with ethyl acetate:hexanes(1:3 to 1:1). Fractions containing the product were combined and concentrated to give compound F (150 mg, 70%) as a white solid. MS (M+H)$^+$ 409.

G) 2,3,4,5-tetrahydro-8-methoxy-2-(1-naphthylsulfonyl)-1H-2-benzazepin-5-amine

Compound F (50 mg, 0.12 mmol) was combined with lithium aluminum hydride (1M in tetrahydrofuran, 1 mL, 1 mmol) in tetrahydrofuran (1 mL). After 0.5 hour, water (20 mL), 1 N aqueous NaOH (10 mL), and ethyl ether (30 mL) were added. The organic layer was separated. The aqueous layer was extracted with ethyl ether and the combined organic layer was dried (MgSO$_4$), filtered and concentrated to give compound G (40 mg, 85%) as a glass. MS: (M+H)$^+$= 383.

H) 2,3,4,5-Tetrahydro-5-[(1H-imidazol-4-ylmethyl)amino]-2-(1-naphthylsulfonyl)-8-methoxy-1H-2-benzazepine, dihydrochloride A solution of compound G (30 mg, 0.78 mmol), 4-formylimidazole (7.5 mg, 0.78 mmol), 1,2-dichloroethane (5 mL) and acetic acid (5 mL) were stirred at room temperature for 30 minutes followed by the addition of sodium triacetoxyborohydride (16 mg, 0.78 mmol). After 18 hours, the mixture was diluted with ethyl acetate (20 mL) and ammonium hydroxide (5 ml), and stirred for an additional 30 minutes. The mixture was extracted with ethyl acetate (2×25 mL), and the combined organic extracts were washed with aqueous sodium bicarbonate (25 ml), followed by aqueous ammonium chloride (25 mL), dried (Na$_2$SO$_4$), and concentrated in vacuo to a semi-solid. This material was purified using reversed phase HPLC. Fractions containing the product were combined and concentrated to dryness. The residue was dissolved in 2N aqueous HCl and concentrated to dryness to provide the title compound (8 mg) as a white solid. MS: (M +H)+=463.

EXAMPLE 12

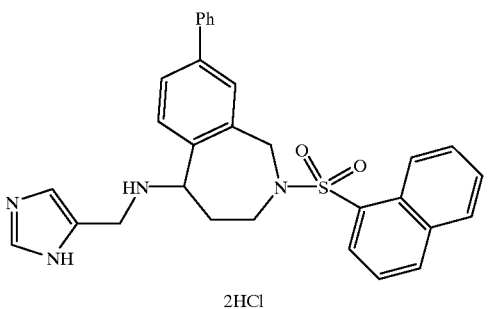

2HCl 2,3,4,5-Tetrahydro-5-[(1H-imidazol-4-ylmethyl)
amino]-2-(1-naphthylsulfonyl)-8-phenyl-1H-2-
benzazepine, dihydrochloride The title compound was prepared as follows.
A) m-phenylbenzyl alcohol To a solution of m-bromobenzyl alcohol (5.0 g, 27 mmol), phenylboronic acid (3.3 g, 27 mmol) and potassium carbonate (9.2 g, 67 mmol) in a mixture of degassed acetone (50 mL) and degassed water (45 mL) under nitrogen was added palladium acetate (12 mg, 0.53 mmol) in degassed acetone (14 mL). The solution was heated to 65° C. for 16 hours under nitrogen. On cooling, ethyl ether (120 mL) was added and the layers were separated. The aqueous layer was washed with ethyl ether. The combined ether layer was washed with brine, dried ($MgSO_4$), filtered and concentrated. The residue was purified by flash chromatography eluting with ethyl acetate:hexanes; 1:10–1:1. Fractions containing the product were combined and concentrated to give compound A (4.9 g), as a white solid.
MS: $(M+H)^+=185$.
B) 3-(m-phenylbenzyl)-N-(1-naphthylsulfonyl) β-alanine methyl ester The title compound (267 mg, 65%) was prepared by reacting compound A with N-(1-naphthalenesulfonyl)-β-alanine methyl ester in a manner similar to the preparation of compound B of Example 11. MS: $(M+H)^+=428$.
C) Preparation of 2,3,4,5-Tetrahydro-5-[(1H-imidazol-4-ylmethyl)amino]-2-(1-naphthylsulfonyl)-8-phenyl-1H-2-benzazepine, dihydrochloride The title compound (10 mg, white solid) was prepared from compound B using the same synthetic sequence as described in the preparation of Example 11.
MS; $(M+H)^+=509$.

EXAMPLE 13

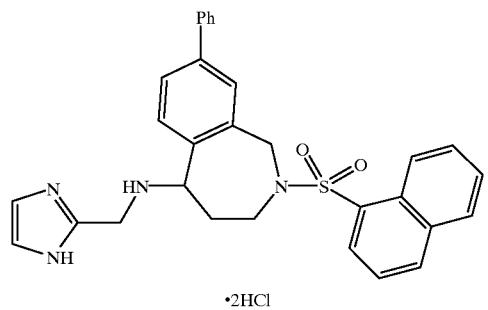

•2HCl 2,3,4,5-Tetrahydro-5-[(1H-imidazol-2-ylmethyl)
amino]-2-(1-naphthylsulfonyl)-8-phenyl-1H-2-
benzazepine, dihydrochloride The title compound (4 mg, white solid) was prepared from an intermediate, 2,3,4,5-tetrahydro-8-phenyl-2-(1-naphthylsulfonyl)-2-benzazepin-5-amine, in the synthesis of Example 12 using the procedure described in step H of Example 11 except that 2-formylimidazole was used in place of 4-formylimidazole. MS; $(M+H)^+=509$.

EXAMPLE 14

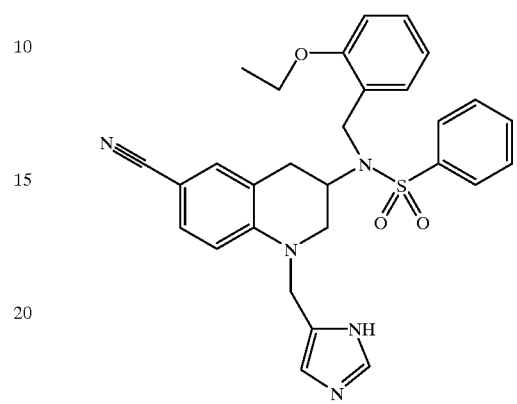

N-[6-Cyano-1,2,3,4-tetrahydro-1-(1H-imidazol-4-
ylmethyl)-3-quinolinyl]-N-[(2-ethoxyphenyl)methyl]
benzenesulfonamide monohydrochloride The title compound was prepared as follows.

A) N-[6-Cyano-1,2,3,4-tetrahydro-1-(1H-imidazol-4-ylmethyl)-3-quinolinyl]benzenesulfonamide Polymer Bound To a solution of Compound F of Example 8 (250 mg, 0.64 mmol) in DMF (3 mL) was added diisopropylethylamine (0.17 mL, 1 mmol) and 2-chlorotrityl chloride resin (0.2 g, 100–200 mesh, 1% DVB, 1 mmol/g loading) and the mixture was shaken for 24 hours. The solvent was removed in vacuo and the residue was washed with 10% triethylamine in dichlormethane. After drying in vacuo, loaded resin (360 mg) was obtained.

B) N-[6-Cyano-1,2,3,4-tetrahydro-1-(1H-imidazol-4-ylmethyl)-3-quinolinyl]-N-[(2-ethoxyphenyl)methyl]-benzenesulfonamide monohydrochloride To a suspension of compound A (30 mg, 0.03 mmol) in dry tetrahydrofuran (1 mL) were added triphenylphosphine (0.26 g, 0.1 mmol), o-ethoxybenzyl alcohol (0.014 mL, 0.1 mmol) and diisopropylazodicarboxylate (0.015 mL, 0.1 mmol) and the mixture was shaken. After 62 hours, the solvent was stripped off. Tetrahydrofuran (1 mL) and another equivalent of the three reagents were added. After 24 hours, the solvent was removed and the resin was washed with dichloromethane. The resin was then shaken with 1:1 mixture of dichloromethane and trifluroaceic acid and triethyl silane (1 mL). The crude product from another reaction (obtained from the reaction on same scale and using Diamide instead of diisopropylazodicarboxylate) was mixed with this one and purified by RP HPLC eluting with aqueous methanol containing 0.1% TFA. The appropriate fractions were concentrated to afford compund A (6 mg, 15%).

LC/MS: $[M+H]^+=528$.

EXAMPLE 15

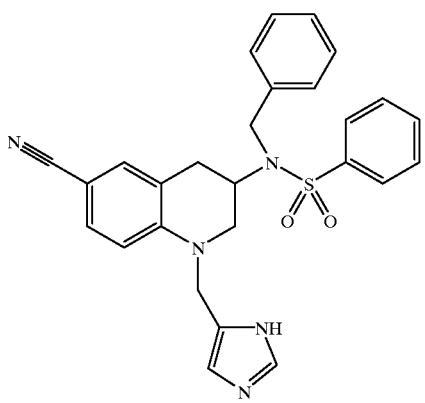

N-[6-Cyano-1,2,3,4-tetrahydro-1-(1H-imidazol-4-ylmethyl)-3-quinolinyl]-N-(phenylmethyl)benzenesulfonamide monohydrochloride The title compound was prepared as follows.
A) N-[6-Cyano-1,2,3,4-tetrahydro-1-[(1-(triphenylmethyl)-1H-imidazol-4-yl]methyl]-3-guinolinyl]benzenesulfonamide The title compound (2.5 g, 75%) was obtained from compound N-[6-Cyano-1,2,3,4-tetrahydro-1-(1H-imidazol-4-ylmethyl)-3-quinolinyl]-N-(phenylmethyl)benzenesulfonamide (2.68 g, 5.3 mmol) in a manner similar to the preparation of N-[6-Bromo-1,2,3,4-tetrahydro-1-[[1-(triphenylmethyl)-1H-imidazol-4-yl]methyl]-3-quinolinyl]methanesulfonamide except dimethylformamide was employed instead of acetonitrile as the solvent. The white solid was used without further purification.
B) N-[6-Cyano-1,2,3,4-tetrahydro-1-(1H-imidazol-4-ylmethyl)-3-quinolinyl]-N-[phenylmethyl]benzenesulfonamide monohydrochloride The title compound was prepared in a manner similar to Compound E of Example 6 except the reaction mixture in the first part was refluxed for 6 hours. A white lyophilate (39 mg, 83%) was obtained.
MS; $(M+H)^+=484$.

Following examples were prepared from N-[6-Cyano-1,2,3,4-tetrahydro-1-[[1-(triphenylmethyl)-1H-imidazol-4-yl]methyl]-3-quinolinyl]benzenesulfonamide in a manner similar to the preparation of Example 15.

EXAMPLE 16

N-[6-Cyano-1,2,3,4-tetrahydro-1-(1H-imidazol-4-ylmethyl)-3-quinolinyl]-N-[(2,3-dimethoxyphenyl)methyl]benzenesulfonamide monohydrochloride

EXAMPLE 17

N-[6-Cyano-1,2,3,4-tetrahydro-1-(1H-imidazol-4-ylmethyl)-3-uinolinyl]-N-[(3,5-dimethylphenyl)methyl]benzenesulfonamide monohydrochloride

EXAMPLE 18

N-[6-Cyano-1,2,3,4-tetrahydro-1-(1H-imidazol-4-ylmethyl)-3-quinolinyl]-N-[(1-naphthalenyl)methyl]benzenesulfonamide monohydrochloride

EXAMPLE 19

N-[6-Cyano-1,2,3,4-tetrahydro-1-(1H-imidazol-4-ylmethyl)-3-quinolinyl]-N-[(2-thiophene)methyl]benzenesulfonamide monohydrochloride

EXAMPLE 20

N-[6-Cyano-1,2,3,4-tetrahydro-1-(1H-imidazol-4-ylmethyl)-3-quinolinyl]-N-[(2,5-dimethylphenyl)methyl]benzenesulfonamide monohydrochloride

EXAMPLE 21

N-[6-Cyano-1,2,3,4-tetrahydro-1-(1H-imidazol-4-ylmethyl)-3-quinolinyl]-N-[(3-thiophene)methyl]benzenesulfonamide monohydrochloride

EXAMPLE 22

N-[6-Cyano-1,2,3,4-tetrahydro-1-(1H-imidazol-4-ylmethyl)-3-quinolinyl]-N-[(3-chlorophenyl)methyl]benzenesulfonamide monohydrochloride

EXAMPLE 23

N-[6-Cyano-1,2,3,4-tetrahydro-1-(1H-imidazol-4-ylmethyl)-3-quinolinyl]-N-[(2-fluorophenyl)methyl]benzenesulfonamide monohydrochloride

EXAMPLE 24

N-[6-Cyano-1,2,3,4-tetrahydro-1-(1H-imidazol-4-ylmethyl)-3-quinolinyl]-N-[(3-pyridyl)methyl]benzenesulfonamide monohydrochloride

EXAMPLE 25

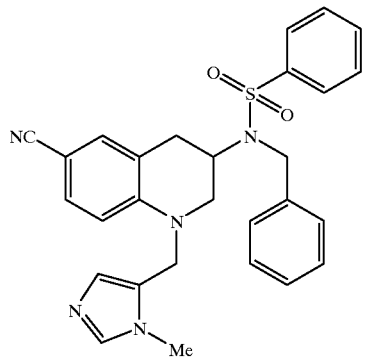

N-[6-Cyano-1,2,3,4-tetrahydro-1-[[1-(methyl)-1H-imidazol-5-yl]methyl]-3-quinolinyl]-N-(phenylmethyl)benzenesulfonamide monohydrochloride The title compound was prepared as follows.
A) N-[6-Cyano-1,2,3,4-tetrahydro-1-[[1-(triphenylmethyl)-1H-imidazol-5-yl]methyl]-3-quinolinyl]-N-(phenylmethyl)-benzenesulfonamide
Example 15 was converted to the title compound in a manner similar to compound A of Example 15.
B) N-[6-Cyano-1,2,3,4-tetrahydro-1-[[1-(methyl)-1H-imidazol-5-yl]methyl]-3-quinolinyl]-N-(phenylmethyl)benzene-sulfonamide monohydrochloride
Compound A (362 mg, 0.5 mmol) was dissolved in THF (5 mL) and cooled to −78° C. To this solution was added methyl triflate (90.2 mg, 0.55 mmol). The mixture was stirred at −78° C. for 0.5 hour and 0° C. for 2 hours. Water (1 mL) and acetic acid (1 mL) were added and the solution was refluxed for 2 hours. The reaction mixture was cooled to rt and neutralized with 1 N NaOH solution. The product was extracted with dichloromethane (3×20 mL) and the combined extract solution was dried ($Na_2SO_4$) and concentrated. The residue was triturated with hexanes (2×10 mL) and purified by silica gel flash column eluting with $CH_2Cl_2$:MeOH:$NH_4OH$/95:5:0.1 to afford the desired product. This material was dissolved in 1 N HCl solution (1 mL) and water (10 mL) and lyophilized to provide the title compound (210 mg, 79%) as a colorless lyophilate.

MS: $(M+H)^+$=498.

EXAMPLE 26

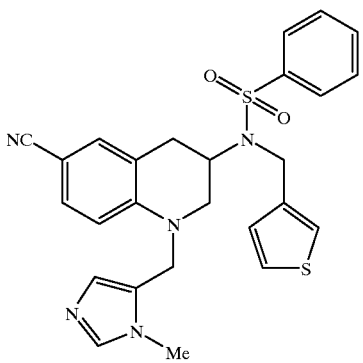

N-[6-Cyano-1,2,3,4-tetrahydro-1-[[1-(methyl)-1H-imidazol-5-yl]methyl]-3-quinolinyl]-N-[(3-thiophenemethyl]benzene-sulfonamide monohydrochloride The title compound was prepared from Example 21 using the same synthetic sequence as described for the preparation of Example 25.

EXAMPLE 27

N-[6-Cyano-1,2,3,4-tetrahydro-1-(1H-imidazol-4-ylmethyl)-3-quinolinyl]-N-(phenylmethyl)methanesulfonamide monohydrochloride The title compound was prepared as follows.

A) N-(6-Bromo-1,2,3,4-tetrahydro-3-quinolinyl) methanesulfonamide

The title compound was prepared from 3-aminoquinoline using the synthetic sequence step C to step E of Example 8. MS; $(M+H)^+$=305.

B) N-(6-Bromo-1,2,3,4-tetrahydro-3-quinolinyl)-N-(phenylmethyl)methanesulfonamide The title compound was prepared by using the procedure described for step A of Example 7. Yield (600 mg, 76%), a white solid. MS; $(M+H)^+$=396.

C) N-[6-Cyano-1,2,3,4-tetrahydro-3-quinolinyl]-N-(phenylmethyl)methanesulfonamide The title compound was prepared by using the procedure described for step B of Example 8. Yield (430 mg, 66%), a white solid. MS; $(M+H)^+$=342.

D) N-[6-Cyano-1,2,3,4-tetrahydro-1-(1H-imidazol-4-ylmethyl)-3-quinolinyl]-N-(phenylmethyl)methanesulfonamide monohydrochloride The title compound was prepared by using the procedure described for step B of Example 10. Yield (30 mg, 66%). MS; $(M+H)^+$=422.

EXAMPLE 28

N-[6-Cyano-1,2,3,4-tetrahydro-1-[[1-(methyl)-1H-imidazol-5-yl]methyl]-3-guinolinyl]-N-(phenylmethyl)methanesulfonamide monohydrochloride The title compound was prepared from Example 27 in a manner similar to the procedure given in step G of Example 29. Yield (35 mg, 80%).

MS $(M+H)^+$=436.

EXAMPLE 29

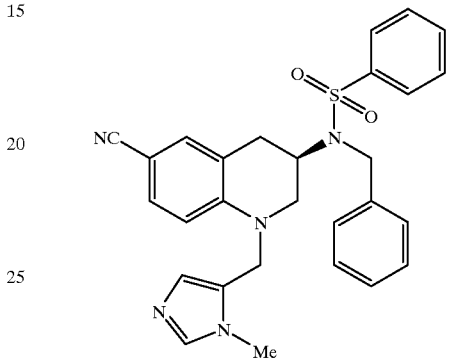

(R)-N-[6-Cyano-1,2,3,4-tetrahydro-1-[[1-(methyl)-1H-imidazol-5-yl]methyl]-3-quinolinyl]-N-(phenylmethyl)benzenesulfonamide monohydrochloride A) (6-Cyano-1,2,3,4-tetrahydro-3-quinolinyl)carbamic acid. 1,1-dimethylethyl ester The title compound was prepared from (6-Bromo-1,2,3,4-tetrahydro-3-quinolinyl)carbamic acid, 1,1-dimethylethyl ester by using the procedure described for step B of Example 8. Yield (140 mg, 67%). MS; $(M+H)^+$=273.

B) 6-Cyano-1,2,3,4-tetrahydro-3-quinolinamine hydrochloride

To a solution of compound A (546 mg, 2 mmol) in methylene chloride (5 mL) at rt was added HCl in dioxane (4 M, 2 mL, 8 mmol). The mixture was stirred at rt for 4 hours. The mixture was concentrated and the residude was triturated with diethyl ether (20 mL). The solid was collected, washed with diethyl ether and dried to afford compound B (420 mg, 100%) as a solid. LC/MS; $(M+H)^+$=174.

C) N-(6-Cyano-1,2,3,4-tetrahydro-3-quinolinyl)-α-hydroxybenzeneacetamide

A mixture of compound B (209 mg, 1 mmol) and N-methylmorphiline (0.5 mL) in DMF (5 mL) was stirred at rt. After 10 min (S)-(+)-mandelic acid (185 mg, 1.2 mmol), HOBt (153 mg, 1 mmol) and EDAC •HCl (230 mg, 1.2 mmol) were added sequentially. The mixture was stirred at rt overnight, diluted with ethyl acetate (20 mL) and was washed with water (2×20 mL). The organic layer was dried ($Na_2SO_4$) and concentrated. The residue was purified by flash column chromatography (SiO2; EtOAc:Hexanes/2:1) to afford a faster moving isomer 1 (120 mg, 39%) as a foam and slower moving isomer 2 (100 mg, 33%) as a solid. The isomer 2 was recrystallized in acetone and analyzed by X-ray single crystal analysis and the structure was determined as (S, S)-configuration.

Isomer 1; [S-(R*,R*)]-N-(6-Cyano-1,2,3,4-tetrahydro-3-quinolinyl)-α-hydroxybenzeneacetamide

[α]$_D$=+54° (c=1.70, MeOH)
$^1$H NMR (CD$_3$OD) 7.23 (m, 2H), 7.14 (m, 3H), 7.03 (m, 2H), 6.37 (d, 1H, J=7.6 Hz), 4.83 (s, 1H), 4.04 (m, 1H), 3.19 (m, 1H), 3.04 (m, 1H), 2.74 (m, 1H), 2.64 (m, 1H).
Isomer 2; [S-(R*,S*)]-N-(6-Cyano-1,2,3,4-tetrahydro-3-quinolinyl)-α-hydroxybenzeneacetamide

[α]$_D$=+99° (c=1.70, MeOH); mp 151–157° C.
$^1$H NMR (CD$_3$OD) 7.29 (m, 7H), 6.57 (d, 1H, J=7.6 Hz), 4.98 (s, 1H), 4.12 (m, 1H), 3.43 (m, 1H), 3.28 (m, 1H), 2.94 (m, 1H), 2.80 (m, 1H).

D) (R)-6-Cyano-1,2,3,4-tetrahydro-3-quinolinamine

A solution of Isomer A (120 mg, 0.39 mmol) in ethanol (1 mL) and 15% sulfuric acid (1 mL) was stirred at reflux temperature for 16 hours. The mixture was cooled to rt and the volatiles were removed in vacuo. Water (2 mL) was added and the solution was washed with methylene chloride once. The aqueous solution was basified with 4 N NaOH to pH 10 and extracted with methylene chloride (3×5 mL). The extracts were combined, dried (Na$_2$SO$_4$) and concentrated to afford compound D (48 mg, 72%) as a solid. LC/MS; (M+H)$^+$=174.

E) (R)-6-Cyano-1,2,3,4-tetrahydro-N-(phenylmethyl)-3-quinolinamine

A mixture of compound D (48 mg, 0.28 mmol) and benzaldehyde (29 mg, 0.28 mmol) in acetic acid was stirred at rt for 15 min and NaBH(OAc)$_3$ (58 mg, 0.28 mmol) was added. The same amounts of benzaldehyde and NaBH(OAc)$_3$ were added after 0.5 hour. The third portion of the same amount of benzaldehyde (29 mg) and NaBH(OAc)$_3$ (58 mg) was added after another 0.5 hours. The reaction mixture was neutrallized with 1 N NaOH solution and extracted with methylene chloride (3×10 mL). The combined extract solution was dried (Na$_2$SO$_4$) and concentrated. The residue was purified by flash column chromatography (SiO$_2$; Ethyl acetate) to afford the title compound (55 mg, 75%) as a gel.

LC/MS; (M+H)$^+$=264.

F) (R)-N-(6-Cyano-1,2,3,4-tetrahydro-3-guinolinyl)-N-(phenylmethyl)benzenesulfonamide A mixture of compound E (55 mg, 0.21 mmol), benzenesulfonyl chloride (55 mg, 0.33 mmol), triethylamine (50 mg, 0.5 mmol) and DMAP (20 mg) in methylene chloride (1 mL) was stirred at rt for 3 hours and then diluted with methylene chloride (10 mL). The resulting mixture was washed with water, dried (MgSO$_4$) and concentrated. The residue was purified by flash column chromatography (SiO$_2$; EtOAc:hexanes/1:2) to afford the title compound (61 mg, 72%) as a foam. LC/MS; (M+H)$^+$=404.

G) (R)-N-[6-Cyano-1,2,3,4-tetrahydro-1-[[1-(methyl)-1H-imidazol-5-yl]methyl]-3-quinolinyl]-N-(phenylmethyl)-benzenesulfonamide monohydrochloride A mixture of compound F (58 mg, 0.14 mmol) and 1-methyl-5-formylimidazole (20 mg, 0.18 mmol) in 1,2-dichloroethane (0.5 mL) and TFA (0.2 mL) was stirred at rt for 5 min and triethylsilane (0.05 mL) was added. The mixture was stirred at rt for 2 hours and concentrated. The residue was purified by reverse phase HPLC (column: YMC S5 ODS 20×100 mm; linear gradient from 10–90% MeOH in water containing 0.1% TFA in 15 min at 20 ml/min; UV 220 nm). Fractions containing the desired product were pooled, concentrated. The residue was dissolved in 1 N HCl solution (0.5 mL) and water (1 mL) and lyophilized to afford the title compound (42 mg, 79%) as a colorless lyophilate. MS; (M+H)$^+$=498. [α]$_D$=+33.2° (c=0.83, MeOH).

EXAMPLE 30

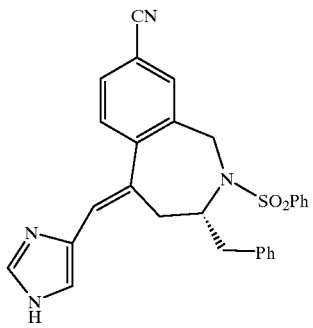

(R,E)-8-Cyano-2,3,4,5-tetrahydro-3-(phenylmethyl)-2-(phenylsulfonyl)-5-[[1H-imidazol-4-yl]methylene]-1H-2-benzazepine monohydrochloride The title compound was prepared as follows.

A) (R)-[3-Hydroxy-1-(phenylmethyl)propyl]carbamic acid 1,1-dimethylethyl ester

To a solution (R)-β-[[(1,1-Dimethylethoxy)carbonyl]amino]-benzenebutanoic acid methyl ester (1.5 g, 5.1 mmol, J. Med. Chem. 1985, 28, 434) in THF (10 mL), was added lithium borohydride (218 mg, 10 mmol), followed by ethanol (10 mL), dropwise. After stirring at rt for 18 hours, an additional lithium borohydride (218 mg 10 mmol) was added and stirring continued for 6 hours. The reaction mixture was ice cooled and adjusted to pH 4 by the addition of a 10% citric acid solution. Organic solvents were removed and the resulting cloudy aqueous solution was extracted with dichloromethane. The extracts were combined, dried (MgSO$_4$) and concentrated in vacuo to afford a clear colorless oil residue which was purified by flash chromatography on silica gel eluting with 30% ethyl acetate in hexanes to yield (1.2 g, 89%) of the title compound as a clear colorless oil.

MS; (M+H)$^+$=266.

B) (R)-[3-Bromo-1-(phenylmethyl)propyl]carbamic acid 1,1-dimethylethyl ester

To a solution of compound A (1.4 g, 4.8 mmol) and carbon tetrabromide (7.9 g, 9.24 mmol) in methylene chloride (50 mL) was added in portions to a solution of triphenylphosphine (2.5 g, 9.6 mmols) over 0.5 hours. The mixture was concentrated in vacuo and the residue was purified by flash chromatography on silica gel. Elution with 10% ethyl acetate in hexane afforded (1.3 g, 83%) of the title compound as a white solid.

MS; (M+H)$^+$=328.

C) (R)-N-[3-Bromo-1-(phenylmethyl)propyl]-benzenesulfonamide

A solution of compound B (1.3 g, 4 mmol) in 4 N HCl in dioxane (30 mL) was stirred for 3 hours. A white precipitate was obtained. The mixture was evaporated to dryness and the residue was washed with ether and dried in vacuo to afford 1.0 g of white solid. To a solution of this solid and triethylamine (1.7 mL, 12 mmol) in methylene chloride (30 mL) was added dropwise benzenesulfonyl chloride (0.56 mL, 4.4 mmol). After 3 hours, the solution was subjected to flash chromatography on silica gel. Elution with 3% ethyl acetate in chloroform afforded (1.33 g, 90%) of the title compound as a colorless oil. MS; M(+H)$^+$=367, 1 Br pattern.

D) (R)-Triphenyl[4-phenyl-3-[(phenylsulfonyl)amino]butyl]-phosphonium bromide

A solution of compound C (1.0 g, 2.7 mmol) and triphenylphosphine (0.78 g, 3 mmol) in of acetonitrile (10 mL)

was heated in a pressure vessel at 125° C. After 20 hours, the mixture was cooled to rt and was added dropwise to 250 mL of vigorously stirred ether. A white precipitate was obtained. Filtration under an atmosphere of nitrogen afforded (1.4 g, 82%) of the title compound as a white powder.

E) (R)-N-[1-(Phenylmethyl)-4-[1-(triphenylmethyl)-1H-imidazol-4-yl]-3-butenyl]benzenesulfonamide A solution of compound D (400 mg, 0.63 mmol) and 1-trityl-4-formylimidazole (320 mg, 0.94 mmol) in methylene chloride was dried over $MgSO_4$. The solids were filtered and the filtrate evaporated to dryness. The white foam residue was diluted with of THF (24 mL) and 3A molecular sieves added. After 1 hour, a solution of lithium bis(trimethylsilyl)amide (1.4 mL, 1M) in THF was added dropwise. After 1 hour, the mixture was filtered and the filtrate was concentrated in vacuo. The residue was diluted with ethyl acetate and the solution washed with brine, dried ($MgSO_4$) and concentrated. The resulting residue was purified by flash chromatography on silica gel. Elution with 40% ethyl acetate in hexane afforded (108 mg) of the title compound, and (149 mg) of the Z-isomer (Combined yield 67%). MS; $(M+H)^+=610$.

F) 4-Bromo-3-(bromomethyl)benzonitrile

To a solution of of 4-bromo-3-methylbenzonitrile (1.0 g, 5.0 mmol) in carbon tetrachloride (7.5 mL) was added N-bromosuccinimide (1.0 g, 5.6 mmol) followed by of benzoylperoxide (50 mg 0.2 mmol) and the mixture was refluxed. After 10 hours, the reaction was cooled to rt, filtered, and the filtrate was washed with 10% $NaHSO_3$ (5 mL) followed by water (5 mL). The organic layer was dried ($Na_2SO_4$), filtered, volatiles removed, and the residue was purified by flash chromatography on silica gel. Elution with 10% Ethyl acetate in hexanes gave the title compound (0.5 g, 36%) as a white solid. $^1H$ NMR (270 MHz, $CDCl_3$) δ 4.55 (s, 2H), 7.38–7.42 (m, 1H), 7.65–7.77 (m, 2H).

G) (R,E)-N-[(2-Bromo-5-cyanophenyl)methyl]-N-[1-(phenylmethyl)-4-[1-(triphenylmethyl)-1H-imidazol-4-yl]-3-butenyl]benzenesulfonamide To a solution of compound E (270 mg, 0.45 mmol) in of THF (4 mL), at rt and under argon, was added dropwise of a 0.5 M solution of potassium bis(trimethylsilyl)amide (1 mL) in toluene. After stirring for 15 min, a solution of compound F (151 mg 0.55 mmol) in THF (1 mL) was added. After 18 hours, the mixture was diluted with ethyl acetate, washed twice with brine, dried ($MgSO_4$), filtered and concentrated. The residue was subjected to flash chromatography on silica gel. Elution with 10% ethyl acetate in hexane afforded the title compound (185 mg, 51%) as a white foam. The compound F (118 mg, 43%). was recovered. MS; $(M+H)^+=803$.

H) (R,E)-8-Cyano-2,3,4,5-tetrahydro-3-(phenylmethyl)-2-(phenylsulfonyl)-5-[[1-(triphenylmethyl)-1H-imidazol-4-yl]methylene]-1H-2-benzazepine A solution of compound G (30 mg, 0.37 mmol), Pd(II) acetate (0.4 mg, 0.002 mmol), triphenyl phosphine (2 mg, 0.008 mmol) and triethylamine (11 µl) in acetonitrile (0.5 mL) was heated at 80° C. for 6 hours. An additional amount of Pd(II) acetate (1 mg) and triphenyl phosphine(4 mg) was then added. After 18 hours the volatiles were removed and the residue subjected to flash chromatography on silica gel. Elution with 35% ethyl acetate in hexane afforded the title compound (20 mg, 75%) as a pale yellow foam. MS; $(M+H)^+=723$.

I) (R,E)-8-Cyano-2,3,4,5-tetrahydro-3-(phenylmethyl)-2-(phenylsulfonyl)-5-[[1H-imidazol-4-yl]methylene]-1H-2-benzazepine monohydrochloride To a solution of compound H (20 mg, 0.027 mmol) in dichloromethane (0.5 mL) was added triethylsilane (0.25 mL) and trifluoroacetic acid (0.1 mL). After 3 hours at rt, the volatiles were removed in vacuo. The white solid residue was diluted with ethyl acetate, a small amount of sat $NaHCO_3$ was added and the mixture was stirred vigorously. The mixture was dried ($MgSO_4$) and concentrated to yield a gummy residue. This material was subjected to flash chromatography on silica gel. Elution with 3% methanol in chloroform afforded the free base of the desired compound as a white solid which was dissolved in ethyl acetate and 1 M HCl in ether (30 µl) was added. The resulting precipitate was filtered and dried in vacuo to afford the title compound (6.5 mg, 47%) as a white solid. MS; $(M+H)^+=481$.

What is claimed is:

1. A compound of the formula I

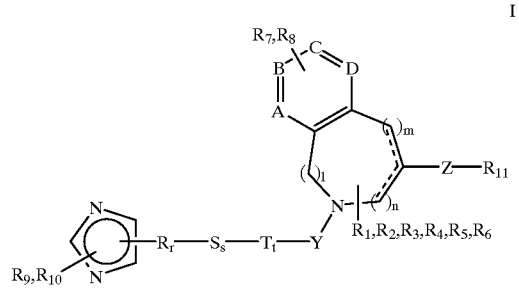

wherein:

r, s and t are 0 or 1;

l is 0; m is 1; n is 1;

Y is selected from the group consisting of $CHR^{12}$, $SO_2$, $SO_3$, $CO_2$, O, $NR^{13}$, $SO_2NR^{14}$, $CONR^{15}$, C(NCN), $C(NCN)NR^{16}$, $NR^{17}CO$, $NR^{18}SO_2$, $CONR^{19}NR^{20}$, $SO_2NR^{21}$ $NR^{22}$, $S(O)(NR^{23})$, $S(NR^{24})(NR^{25})$, or without Y;

Z is selected from the group consisting of S, SO, $SO_2$, $SO_3$, CO, $CO_2$, O, $NR^{13}$, $SO_2NR^{14}$, $CONR^{15}$, $NR^{26}NR^{27}$, $ONR^{28}$, $NR^{29}O$, $NR^{30}SO_2NR^{31}$, $NR^{32}SO_2$, $NR^{33}C(NCN)$, $NR^{34}C(NCN)NR^{35}$, $NR^{36}CO$, $NR^{37}CONR^{38}$, $NR^{39}CO_2$, $OCONR^{40}$, $S(O)(NR^{41})$, or $S(NR^{42})(NR^{43})$;

$R^7$, $R^8$ are selected from the group consisting of hydrogen, halo, nitro, cyano and $U-R^{44}$;

U is selected from the group consisting of S, O, $NR^{45}$, CO, SO, $SO_2$, $CO_2$, $NR^{46}CO_2$, $NR^{47}CONR^{48}$, $NR^{49}SO_2$, $NR^{50}SO_2NR^{51}$, $SO_2NR^{52}$, $NR^{53}CO$, $CONR^{54}$, $PO_2R^{55}$ and $PO_3R^{56}$ or without U;

$R^9$, $R^{10}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$ and $R^{59}$ are selected from the group consisting of hydrogen, lower alkyl, aryl, heterocyclo, substituted alkyl or aryl;

$R^{11}$ and $R^{44}$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo;

$R^1$, $R^2$, $R^3$ $R^4$, $R^5$ and $R^6$ are selected from the group consisting of hydrogen, alkyl, substituted alkyl, alkenyl, substituted alkenyl, alkynyl, substituted alkynyl, aralkyl, cycloalkyl, aryl, substituted aryl, heterocyclo, substituted heterocyclo, cyano, alkoxycarbonyl, carboxy, carbamyl, substituted carbamyl wherein substituents on the nitrogen of the substituted carbamyl are selected hydrogen, alkyl, substituted alkyl, aryl or aralkyl, substituted aryl, heterocyclo, substituted heterocyclo; any two of $R^1, R^2, R^3, R^4, R^5$ and $R^6$ can join to form a cycloalkyl group; any two of $R^1, R^2, R^3, R^4, R^5$ and $R^6$ together can be oxo, except when the carbon atom bearing the substituent is part of a double bond;

R, S and T are selected from the group consisting of $CH_2$, and $CH(CH_2)_pQ$ wherein Q is $NR^{57}R^{58}$, $OR^{59}$, or CN; wherein p is 0, 1 or 2; and A, B, C and D are carbon; its enantiomers, diastereomers, pharmaceutically acceptable salts and solvates thereof; with the provisos that:

$R^{11}$ may be hydrogen except when Z is SO, or when Z is O, $NR^{13}$ or S and the carbon to which it is attached is part of a double bond or when Y is $SO_2$, $CO_2$, $NR^{18}SO_2$, $S(O)(NR^{23})$, or $S(NR^{24})(NR^{25})$; and $R^{44}$ may be hydrogen except when U is SO, $SO_2$, $NR^{46}CO_2$ or $NR^{49}SO_2$.

2. The compound of claim 1, wherein l, m, r, s and t are 0 or 1; n is 1 or 2;

Y is $CHR^{12}$, $SO_2$, $SO_3$, $CO_2$, $SO_2NR^{14}$, $CONR^{15}$ or without Y;

Z is $SO_2$, $SO_3$, CO, $CO_2$, $NR^{13}$, $SO_2NR^{14}$, $CONR^{15}$, $NR^{30}SO_2NR^{31}$, $NR^{32}SO_2$, $NR^{36}CO$, $NR^{37}CONR^{38}$, or $NR^{39}CO_2$.

3. The compound of claim 2, of the formula I, wherein l, r, s, and t is 0;

Y is $CHR^{12}$, $SO_2$, $SO_2NR^{14}$, or $CONR^{15}$ or without Y; and

Z is $SO_2$, $SO_3$, CO, $CO_2$, $SO_2NR^{14}$, $CONR^{15}$, $NR^{30}SO_2NR^{31}$, $NR^{32}SO_2$, $NR^{36}CO$, $NR^{37}$ or $CONR^{38}$, $NR^{39}CO_2$.

4. The compound of claim 3, wherein $R^7$, $R^8$ is halogen, nitro, cyano or $U-R^{44}$ wherein U is S, O, $NR^{46}CO_2$, $NR^{47}CONR^{48}$, $R^{44}$ is hydrogen, alkyl, substituted alkyl, alkenyl, substituted alkenyl, alkynyl, substituted alkynyl, aralkyl, cycloalkyl, aryl, substituted aryl, heterocyclo or substituted heterocyclo, $R^{46}$ and $R^{47}$ is hydrogen, lower alkyl, aryl substituted alkyl or aryl and.

5. The compound of claim 1, wherein the salt is of an organic or inorganic acid.

6. The compound of claim 5, wherein the salt is of hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid, nitric acid, phosphoric acid, boric acid, tartaric acid, citric acid, succinic acid, benzoic acid, ascorbic acid or salicyclic acid.

7. The compound of claim 1, which is:

N-[6-bromo-1,2,3,4-tetrahydro-1-(1H-imidazol-4-ylmethyl)-3-quinolinyl]-1-naphthalenesulfonamide, dihydrochloride;

N-[6-bromo-1,2,3,4-tetrahydro-1-(1H-imidazol-4-ylmethyl)-3-quinolinyl]-1-naphthalenecarboxamide, dihydrochloride;

N-[6-bromo-1,2,3,4-tetrahydro-1-(1H-imidazol-4-ylmethyl)-3-quinolinyl]-N-(phenylmethyl)methanesulfonamide, dihydrochloride;

N-[6-bromo-1,2,3,4-tetrahydro-1-(1H-imidazol-4-ylmethyl)-3-quinolinyl]benzenesulfonamide, dihydrochloride;

N-[6-bromo-1,2,3,4-tetrahydro-1-(1H-imidazol-4-ylmethyl)-3-quinolinyl]-N-(phenylmethyl)acetamide, dihydrochloride;

N-[6-bromo-1,2,3,4-tetrahydro-1-(1H-imidazol-4-ylmethyl)-3-quinolinyl]-N-(4-methoxyphenyl)methyl]methanesulfonamide, monohydrochloride;

N-[6-bromo-1,2,3,4-tetrahydro-1-(1H-imidazol-4-ylmethyl)-3-quinolinyl]-N-[(4-methylphenyl)methyl]methanesulfonamide monohydrochloride;

N-[6-cyano-1,2,3,4-tetrahydro-1-(1H-imidazol-4-ylmethyl)-3-quinolinyl]-N-[(3-methylphenyl)methyl]benzenesulfonamide monohydrochloride;

N-[6-cyano-1,2,3,4-tetrahydro-1-(1H-imidazol-4-ylmethyl)-3-quinolinyl]-N-[(2-methylphenyl)methyl]benzenesulfonamide monohydrochloride;

N-[6-cyano-1,2,3,4-tetrahydro-1-(1H-imidazol-4-ylmethyl)-3-quinolinyl]-N-(phenylethyl)benzenesulfonamide monohydrochloride;

N-[6-Cyano-1,2,3,4-tetrahydro-1-(1H-imidazol-4-ylmethyl)-3-quinolinyl]-N-[(2-ethoxyphenyl)methyl]benzenesulfonamide monohydrochloride;

N-[6-Cyano-1,2,3,4-tetrahydro-1-(1H-imidazol-4-ylmethyl)-3-quinolinyl]-N-(phenylmethyl)benzenesulfonamide monohydrochloride;

N-[6-Cyano-1,2,3,4-tetrahydro-1-(1H-imidazol-4-ylmethyl)-3-quinolinyl]-N-[(2,3-dimethoxyphenyl)methyl]benzenesulfonamide monohydrochloride;

N-[6-Cyano-1,2,3,4-tetrahydro-1-(1H-imidazol-4-ylmethyl)-3-quinolinyl]-N-[(3,5-dimethylphenyl)methyl]benzenesulfonamide monohydrochloride;

N-[6-Cyano-1,2,3,4-tetrahydro-1-(1H-imidazol-4-ylmethyl)-3-quinolinyl]-N-[(1-naphthalenyl)methyl]benzenesulfonamide monohydrochloride;

N-[6-Cyano-1,2,3,4-tetrahydro-1-(1H-imidazol-4-ylmethyl)-3-quinolinyl]-N-[(2-thiophene)methyl]benzenesulfonamide monohydrochloride;

N-[6-Cyano-1,2,3,4-tetrahydro-1-(1H-imidazol-4-ylmethyl)-3-quinolinyl]-N-[(2,5-dimethylphenyl)methyl]benzenesulfonamide monohydrochloride;

N-[6-Cyano-1,2,3,4-tetrahydro-1-(1H-imidazol-4-ylmethyl)-3-quinolinyl]-N-[(3-thiophene)methyl]benzenesulfonamide monohydrochloride;

N-[6-Cyano-1,2,3,4-tetrahydro-1-(1H-imidazol-4-ylmethyl)-3-quinolinyl]-N-[(3-chlorophenyl)methyl]benzenesulfonamide monohydrochloride;

N-[6-Cyano-1,2,3,4-tetrahydro-1-(1H-imidazol-4-ylmethyl)-3-quinolinyl]-N-[(2-fluorophenyl)methyl]benzenesulfonamide monohydrochloride;

N-[6-Cyano-1,2,3,4-tetrahydro-1-(1H-imidazol-4-ylmethyl)-3-quinolinyl]-N-[(3-pyridyl)methyl]benzenesulfonamide monohydrochloride;

N-[6-Cyano-1,2,3,4-tetrahydro-1-[[1-(methyl)-1H-imidazol-5-yl]methyl]-3-quinolinyl]-N-(phenylmethyl)benzenesulfonamide monohydrochloride;

N-[6-Cyano-1,2,3,4-tetrahydro-1-[[1-(methyl)-1H-imidazol-5-yl]methyl]-3-quinolinyl]-N-[(3-thiophenemethyl]benzenesulfonamide monohydrochloride;

N-[6-Cyano-1,2,3,4-tetrahydro-1-(1H-imidazol-4-ylmethyl)-3-quinolinyl]-N-(phenylmethyl)methanesulfonamide monohydrochloride;

N-[6-Cyano-1,2,3,4-tetrahydro-1-[[1-(methyl)-1H-imidazol-5-yl]methyl]-3-quinolinyl]-N-(phenylmethyl)methanesulfonamide monohydrochloride;

(R)-N-[6-Cyano-1,2,3,4-tetrahydro-1-[[1-(methyl)-1H-imidazol-5-yl]methyl]-3-quinolinyl]-N-(phenylmethyl)benzenesulfonamide monohydrochloride.

8. A pharmaceutical composition comprising a pharmaceutical carrier and a therapeutically effective amount of a compound of claim 1.

9. A method of inhibiting tumors which comprises administering to a mammalian subject an effective tumor inhibiting amount of a compound of claim 1.

* * * * *